United States Patent
Zimmerman et al.

(10) Patent No.: US 11,801,273 B2
(45) Date of Patent: Oct. 31, 2023

(54) COMPOSITIONS AND METHODS TO INCREASE PRODUCTION OF ISOTHIOCYANATES

(71) Applicant: Church & Dwight Co., Inc., Princeton, NJ (US)

(72) Inventors: Noah Paul Zimmerman, Chapel Hill, NC (US); Amy Wescott, Rubicon, WI (US)

(73) Assignee: Church & Dwight Co., Inc., Princeton, NJ (US)

(*) Notice: Subject to any disclaimer, the term of this patent is extended or adjusted under 35 U.S.C. 154(b) by 0 days.

(21) Appl. No.: 17/558,025

(22) Filed: Dec. 21, 2021

(65) Prior Publication Data
US 2022/0193152 A1 Jun. 23, 2022

Related U.S. Application Data

(60) Provisional application No. 63/129,897, filed on Dec. 23, 2020.

(51) Int. Cl.
*A61K 35/742* (2015.01)
*C12N 1/20* (2006.01)
*C12R 1/125* (2006.01)

(52) U.S. Cl.
CPC ............ *A61K 35/742* (2013.01); *C12N 1/205* (2021.05); *C12R 2001/125* (2021.05)

(58) Field of Classification Search
CPC .... A61K 35/742; C12N 1/205; C12N 9/2402; C12R 2001/125; C12R 2001/46; C12P 11/00; C12P 13/00; C12Y 302/01147
See application file for complete search history.

(56) References Cited

U.S. PATENT DOCUMENTS

| 5,882,646 A | 3/1999 | Pusateri et al. |
| 8,927,007 B2 | 1/2015 | Talalay et al. |

(Continued)

FOREIGN PATENT DOCUMENTS

| CN | 104273404 | 1/2015 |
| CN | 110946996 | 4/2020 |

(Continued)

OTHER PUBLICATIONS

Hong, Huynh A., et al. "Bacillus subtilis isolated from the human gastrointestinal tract." Research in microbiology 160.2 (2009): 134-143. (Year: 2009).*

(Continued)

*Primary Examiner* — Lora E Barnhart Driscoll
*Assistant Examiner* — Candice Lee Swift
(74) *Attorney, Agent, or Firm* — Womble Bond Dickinson (US) LLP

(57) ABSTRACT

Compositions and methods for converting at least one glucosinolate to an isothiocyanate using *Bacillus subtilis* 839, *Bacillus subtilis* CO4_4, *Pediococcus pentosaceus* M3_H01, and/or *Pediococcus pentosaceus* M2_H12, or active variants thereof, are provided. Conversion of glucosinolates, such as glucoraphanin, to isothiocyanates, such as sulforaphane, leads to the stimulation of the Nrf2/Keap pathway and phase II enzymes, providing chemoprotective and anti-inflammatory effects. Accordingly, provided herein are compositions comprising *Bacillus subtilis* 839, *Bacillus subtilis* CO4_4, *Pediococcus pentosaceus* M3_H01, and/or *Pediococcus pentosaceus* M2_H12, or active variants thereof, for administration to subjects for increasing isothiocyanate (e.g., sulforaphane) production, increasing the expression of genes regulated by the Nrf2 transcription factor, including phase II enzymes, decreasing inflammation, and treating or preventing an inflammatory disorder or (Continued)

a cancer. The composition can comprise at least one glucosinolate or a plant, plant part or an extract thereof comprising glucosinolate(s).

20 Claims, 4 Drawing Sheets

Specification includes a Sequence Listing.

(56) References Cited

U.S. PATENT DOCUMENTS

| | | |
|---|---|---|
| 8,937,050 B2 | 1/2015 | Talalay |
| 9,017,666 B2 | 4/2015 | Ashurst et al. |
| 9,421,183 B2 | 8/2016 | Cornblatt et al. |
| 10,195,171 B2 | 2/2019 | Kosi-Kupe |
| 10,307,390 B2 | 6/2019 | Damireddi et al. |
| 10,314,865 B2 | 6/2019 | Kovarik et al. |
| 10,485,258 B2 | 11/2019 | Raskin et al. |
| 10,583,178 B2 | 3/2020 | Cornblatt et al. |
| 2008/0311192 A1 | 12/2008 | West et al. |
| 2017/0245500 A1 | 8/2017 | Barker |
| 2019/0069586 A1 | 3/2019 | Kyle et al. |
| 2019/0209625 A1 | 7/2019 | Chang et al. |
| 2022/0160802 A1 | 5/2022 | Augustin et al. |

FOREIGN PATENT DOCUMENTS

| | | |
|---|---|---|
| FR | 2827774 | 6/2005 |
| WO | 2017077139 | 5/2017 |
| WO | 2018217588 | 11/2018 |
| WO | 2019060963 | 4/2019 |
| WO | 2020038898 | 2/2020 |
| WO | 2020161653 | 8/2020 |
| WO | 2020198808 | 10/2020 |
| WO | 2021022336 | 2/2021 |

OTHER PUBLICATIONS

ARM & HAMMER; https://ahfoodchain.com/en/about/news/2019/11/new-bacillus-strains; accessed Jun. 2, 2023 (Year: 2019).*
Fahey, et al., "Bioavailability of Sulforaphane Following Ingestion of Clucoraphanin-Rich Broccoli Sprout and See Extracts with Active Myrosinase: a Pilot Study of the Effects of Proton Pump Inhibitor Administration",Nutrients (2019), vol. 11, 1489, pp. 1-14. CH.
Luang-In, et al., "Formation of Sulforaphane and Iberin Products from Thai Cabbage Fermented by Myrosinase-Positive Bacteria", Molecules (2018), vol. 23, 955, pp. 1-14. CH.
Mullaney, et al., "Lactic acid bacteria convert glucosinolates to nitriles efficiently yet differently from Enterobacteriaceae", J. Agric. Food Chem. (2013), vol. 61, Issue 12, pp. 3039-3046. NZ.
Narbad, et al., "Gut Glucosinolate Metabolism and Isothiocyanate Production", Mol. Nutr. Food Res (2018), vol. 62, 1700991, pp. 1-10. GB.
Tian, et al., "Microbiota: a mediator to transform glucosinolate precursors in cruciferous vegetables to the active isothiocyanates", Journal of the Science of Food and Agriculture, vol. 98, Issue 4 (2018), pp. 1255-1260. US.

* cited by examiner

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Synthetic sequence

<400> SEQUENCE: 1
atcatgtttc tggcattgcg tgcc                                            24

<210> SEQ ID NO 2
<211> LENGTH: 22
<212> TYPE: DNA
<213> ORGANISM: Artificial Sequence
<220> FEATURE:
<223> OTHER INFORMATION: Synthetic sequence

<400> SEQUENCE: 2
gttgataagc gcgttggtaa tc                                              22

<210> SEQ ID NO 3
<211> LENGTH: 20
<212> TYPE: DNA
<213> ORGANISM: Artificial Sequence
<220> FEATURE:
<223> OTHER INFORMATION: Synthetic sequence

<400> SEQUENCE: 3
cgtatcgtgg gctggtaaag                                                 20

<210> SEQ ID NO 4
<211> LENGTH: 24
<212> TYPE: DNA
<213> ORGANISM: Artificial Sequence
<220> FEATURE:
<223> OTHER INFORMATION: Synthetic sequence

<400> SEQUENCE: 4
cgcgccaacc tgtagctcaa attc                                            24

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence

<400> SEQUENCE: 5
gttcaccacc tcgcgtatat c                                               21

```
<210> SEQ ID NO 6
<211> LENGTH: 20
<212> TYPE: DNA
<213> ORGANISM: Artificial Sequence
<220> FEATURE:
<223> OTHER INFORMATION: Synthetic sequence

<400> SEQUENCE: 6
cttgccggtg gagatgttta                                              20

<210> SEQ ID NO 7
<211> LENGTH: 18
<212> TYPE: DNA
<213> ORGANISM: Artificial Sequence
<220> FEATURE:
<223> OTHER INFORMATION: Synthetic sequence

<400> SEQUENCE: 7
agagtttgat tggctcag                                                18

<210> SEQ ID NO 8
<211> LENGTH: 15
<212> TYPE: DNA
<213> ORGANISM: Artificial Sequence
<220> FEATURE:
<223> OTHER INFORMATION: Synthetic sequence

<400> SEQUENCE: 8
taccttgtta gactt                                                   15

<210> SEQ ID NO 9
<211> LENGTH: 1473
<212> TYPE: DNA
<213> ORGANISM: Lactobacillus plantarum
<220> FEATURE:
<221> NAME/KEY: misc_feature
<222> LOCATION: (1)..(1473)
<223> OTHER INFORMATION: Glycosyl hydrolase coding sequence

<400> SEQUENCE: 9
atgcaatttc cggctgattt ttactggggt ggggctactg ccgctaatca atgcgaaggt      60
gcttatgatg ttgatggtcg gggcctgact atgaaggata ttacgacaat gggaggcctt     120
aatcagcgac ggcaagtcac ttatttgcaa gcggatggta ctcctggaaa aggggattca     180
attcctgctg gagcacacgg agcggtactg ccagatgact attatcctaa tcagactagt     240
attgacttct atcatcgata tcaagaagat gttgcgctgt ttgcagagat gggtttcaaa     300
atgtatcgaa tgtcgatttc ctggtcacgg attttcccac gcggcgatga aaatgaacct     360
aatcaagcag ggttggattt ttatcgccag gtgttcgaaa ctttgaaaaa atatgaaatt     420
gaaccattgg tgacgatttc acacttcgat atgccactgt atctggagga acgtatggt      480 ggctggaatg accgtcggat gattggtttt taccagcatt atgcggaaac gctatttacg     540
gcgtatcgtg ggctggtaaa gcactggatt accttcaatg aaattaataa tacgatcatg     600
tttctggcat tgcgtgccaa agccggtgat gcagattacc aacgcgctta tcaacaatta     660
cattatcaat ttgtcgctag tgctttagcc gtacagcaag cacatgcgat tgatggcgaa     720
aataaagttg gttgcatgat ttgcggtatc acgtcttatc cgttaacctg tgatccggcg     780
gatgtcttgc agaatcggta cgtctgggaa caaaacatct attactgtgg tgatgtgcag     840
tgccagggac agtatccaac ctatgcacga cgtttatgga atgagcatca agttgattta     900
```

```
gacattacgg acagtgattt agaagccttg aaagccggta cggttgactg gtataccttt    960
tcgtattaca tgtcaacggc agttacaaca catgaggtca gtgcaactgt tggcggtaat   1020
ttttcgatgg gcgcgcgtaa cccatatcta caatactctg aatgggagtg gcggatgac   1080 ccggctggtc tacaaatatta tttggagctg atgaatgatc gatatcattt accactaatg   1140
gttgttgaaa atggattggg tgccaaggat tatttgacag tagatggtca aatccatgat   1200
gtataccgga ttagctatct acgtaaacat attcaagcaa tggcaacggc aattcaccat   1260
ggcgtcaaac tgattggtta taccagttgg ggctgtattg atttagtttc tgcaggtaca   1320
gggcaaatgt ctaaacgata cggattgatt tatgtggatc gtcaagacga tggtagtgga   1380
actctggccc gaatcccgaa ggactctttc tactggtatc agcgagtgat tgcatccaat   1440
ggtcaagatc tgggtccctc ggcctcaaat taa                                1473
```

<210> SEQ ID NO 10
<211> LENGTH: 490
<212> TYPE: PRT
<213> ORGANISM: Lactobacillus plantarum
<220> FEATURE:
<221> NAME/KEY: MISC_FEATURE
<222> LOCATION: (1)..(490)
<223> OTHER INFORMATION: glycosyl hydrolase

<400> SEQUENCE: 10

```
Met Gln Phe Pro Ala Asp Phe Tyr Trp Gly Gly Ala Thr Ala Ala Asn
1               5                   10                  15

Gln Cys Glu Gly Ala Tyr Asp Val Asp Gly Arg Gly Leu Thr Met Lys
            20                  25                  30

Asp Ile Thr Thr Met Gly Gly Leu Asn Gln Arg Arg Gln Val Thr Tyr
        35                  40                  45

Leu Gln Ala Asp Gly Thr Pro Gly Lys Gly Asp Ser Ile Pro Ala Gly
    50                  55                  60

Ala His Gly Ala Val Leu Pro Asp Asp Tyr Tyr Pro Asn Gln Thr Ser
65                  70                  75                  80

Ile Asp Phe Tyr His Arg Tyr Gln Glu Asp Val Ala Leu Phe Ala Glu
                85                  90                  95

Met Gly Phe Lys Met Tyr Arg Met Ser Ile Ser Trp Ser Arg Ile Phe
            100                 105                 110

Pro Arg Gly Asp Glu Asn Glu Pro Asn Gln Ala Gly Leu Asp Phe Tyr
        115                 120                 125

Arg Gln Val Phe Glu Thr Leu Lys Lys Tyr Glu Ile Glu Pro Leu Val
    130                 135                 140

Thr Ile Ser His Phe Asp Met Pro Leu Tyr Leu Glu Glu Thr Tyr Gly
145                 150                 155                 160

Gly Trp Asn Asp Arg Arg Met Ile Gly Phe Tyr Gln His Tyr Ala Glu
                165                 170                 175

Thr Leu Phe Thr Ala Tyr Arg Gly Leu Val Lys His Trp Ile Thr Phe
            180                 185                 190

Asn Glu Ile Asn Asn Thr Ile Met Phe Leu Ala Leu Arg Ala Lys Ala
        195                 200                 205

Gly Asp Ala Asp Tyr Gln Arg Ala Tyr Gln Leu His Tyr Gln Phe
    210                 215                 220

Val Ala Ser Ala Leu Ala Val Gln Gln Ala His Ala Ile Asp Gly Glu
225                 230                 235                 240

Asn Lys Val Gly Cys Met Ile Cys Gly Ile Thr Ser Tyr Pro Leu Thr
                245                 250                 255
```

```
-continued

Cys Asp Pro Ala Asp Val Leu Gln Asn Arg Tyr Val Trp Glu Gln Asn
            260                 265                 270

Ile Tyr Tyr Cys Gly Asp Val Gln Cys Gln Gly Gln Tyr Pro Thr Tyr
        275                 280                 285

Ala Arg Arg Leu Trp Asn Glu His Gln Val Asp Leu Asp Ile Thr Asp
    290                 295                 300

Ser Asp Leu Glu Ala Leu Lys Ala Gly Thr Val Asp Trp Tyr Thr Phe
305                 310                 315                 320

Ser Tyr Tyr Met Ser Thr Ala Val Thr Thr His Glu Val Ser Ala Thr
                325                 330                 335

Val Gly Gly Asn Phe Ser Met Gly Ala Arg Asn Pro Tyr Leu Gln Tyr
            340                 345                 350

Ser Glu Trp Glu Trp Ala Asp Asp Pro Ala Gly Leu Gln Tyr Tyr Leu
        355                 360                 365

Glu Leu Met Asn Asp Arg Tyr His Leu Pro Leu Met Val Val Glu Asn
    370                 375                 380

Gly Leu Gly Ala Lys Asp Tyr Leu Thr Val Asp Gly Gln Ile His Asp
385                 390                 395                 400

Val Tyr Arg Ile Ser Tyr Leu Arg Lys His Ile Gln Ala Met Ala Thr
                405                 410                 415

Ala Ile His His Gly Val Lys Leu Ile Gly Tyr Thr Ser Trp Gly Cys
            420                 425                 430

Ile Asp Leu Val Ser Ala Gly Thr Gly Gln Met Ser Lys Arg Tyr Gly
        435                 440                 445

Leu Ile Tyr Val Asp Arg Gln Asp Asp Gly Ser Gly Thr Leu Ala Arg
    450                 455                 460

Ile Pro Lys Asp Ser Phe Tyr Trp Tyr Gln Arg Val Ile Ala Ser Asn
465                 470                 475                 480

Gly Gln Asp Leu Gly Pro Ser Ala Ser Asn
                485                 490
```

COMPOSITIONS AND METHODS TO INCREASE PRODUCTION OF ISOTHIOCYANATES

RELATED APPLICATIONS

This application claims priority to U.S. Provisional Application No. 63/129,897, filed on Dec. 23, 2020, the contents of which are incorporated by reference herein.

SEQUENCE LISTING

This application contains a Sequence Listing which is submitted herewith in electronically readable format. The Sequence Listing file was created on Dec. 21, 2021, is named "C63806 2880WO_SL.txt" and its size is 8.04 kb. The entire contents of the Sequence Listing in the sequence-listing.txt file are incorporated by reference herein

FIELD OF THE INVENTION

The invention relates to microbial compositions for increasing the production of isothiocyanates from glucosinolates

BACKGROUND OF THE INVENTION

The health benefits of a diet rich in cruciferous plants is due not only to the vitamins, minerals and fiber found in the plants but also to compounds such as glucosinolates. Glucosinolates such as glucoraphanin, found in foods like broccoli, kale, and cabbage are well known for providing health benefits such as reduced risk of certain types of cancer as well as neurodegenerative disorders (Mullaney et al., 2013, *J. Agric. Food Chem.* 61:3039-3046 and Zhang et al., 2017, *Front. Aging Neurosci.* 9:121). However, multiple studies demonstrate that many of these glucosinolates are poorly absorbed into the body (Marin et al., 2015, *BioMed Res. Int.* 1-18). Recent work demonstrates that the majority of benefits may come from the smaller, more well absorbed bacterial metabolites rather than from the parent compound (Selma et al., 2009, *J Agric. Food Chem.* 57:6485-6501).

While highly abundant, glucosinolates like glucoraphanin provide little benefit until broken down by an endogenous enzyme, myrosinase. Myrosinase is released upon rupture of the plant cells such as chopping or chewing, and glucosinolates are hydrolyzed into isothiocyanates (for example, glucoraphanin is hydrolyzed into sulforaphane) (Fahey et al., 2015, *PLoS ONE* e0140963 and Atwell et al., 2015, *Mol. Nutr. Food. Res.* 59:424-433). Isothiocyanates (e.g., sulforaphane) not only benefit the plant by providing a defense system against insects, but also provides many health benefits to humans. Isothiocyanates like sulforaphane have been shown to induce phase II enzymes, promoting carcinogen metabolism and excretion (Mullaney, et al., 2013). In addition, more recent work has shown that isothiocyanates (e.g., sulforaphane) have the potential to inhibit histone deacetylases (HDACs) by competitive inhibition (Atwell et al., 2015). HDAC inhibition was followed by the induction of G2/M phase cell cycle arrest and apoptosis of cancer cells. Isothiocyanates (e.g., sulforaphane) have both a chemoprotective effect through phase II enzyme induction and the promotion of cancer cell death through apoptosis.

While glucosinolate conversion to isothiocyanates is catalyzed by the myrosinase enzyme present in the vegetable, cooking of the vegetable causes denaturation of the enzyme and glucosinolates can no longer be hydrolyzed into isothiocyanates.

BRIEF SUMMARY OF THE INVENTION

Compositions and methods for converting at least one glucosinolate to an isothiocyanate using *Bacillus subtilis* 839, *Bacillus subtilis* CO4_4, *Pediococcus pentosaceus* M3_H01, and/or *Pediococcus pentosaceus* M2_H12, or active variants thereof, are provided. Conversion of the glucosinolate to an isothiocyanate compound leads to the stimulation of the Nrf/Keap pathway and phase II enzymes, providing chemoprotective and anti-inflammatory effects. Accordingly, provided herein are compositions comprising *Bacillus subtilis* 839, *Bacillus subtilis* CO4_4, *Pediococcus pentosaceus* M3_H01, and/or *Pediococcus pentosaceus* M2_H12, or active variants thereof, for administration to subjects for increasing isothiocyanate (e.g., sulforaphane) production, including in the gut, increasing the expression of genes regulated by the Nrf2 transcription factor, including phase II enzymes, decreasing inflammation, and treating an inflammatory disorder or a cancer. The composition can comprise at least one glucosinolate such as a cruciferous plant, plant part, or an extract thereof.

Non-limiting embodiments include:
1. A bacterial strain composition comprising:
    (a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
    (b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof;
    wherein said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof is present at about $10^6$ CFU/gram to about $10^{10}$ CFU/gram or at about $10^6$ CFU/ml to about $10^{10}$ CFU/ml.
2. The bacterial strain composition of embodiment 1, wherein said bacterial cell, spore, forespore, or combination of cells, forespores, and/or spores, or the active variant thereof is present at about $10^8$ CFU/gram to about $10^{10}$ CFU/gram or at about $10^8$ CFU/ml to about $10^{10}$ CFU/ml.
3. The bacterial strain composition of embodiment 1 or 2, further comprising at least one glucosinolate.
4. The bacterial strain composition of embodiment 3, wherein said composition comprises at least one plant, plant part or extract thereof comprising said at least one glucosinolate.
5. The bacterial strain composition of embodiment 4, wherein said glucosinolate comprises glucoraphanin.
6. The bacterial strain composition of embodiment 4 or 5, wherein said plant extract comprises an extract from at least one cruciferous plant or said at least one plant or plant part comprises a cruciferous plant or plant part.
7. The bacterial strain composition of embodiment 6, wherein said at least one cruciferous plant or plant part is selected from the group consisting of broccoli, cauliflower, and Brussels sprouts.

8. The bacterial strain composition of any one of embodiments 1-7, wherein an effective amount of said bacterial strain composition increases conversion of at least one glucosinolate to an isothiocyanate.
9. The bacterial strain composition of embodiment 8, wherein said glucosinolate comprises glucoraphanin and said isothiocyanate comprises sulforaphane.
10. A bacterial strain composition comprising:
   (a) at least one glucosinolate; and
   (b) a bacterial strain comprising:
      (i) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
      (ii) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof.
11. The bacterial strain composition of embodiment 10, wherein said at least one glucosinolate comprises glucoraphanin.
12. The bacterial strain composition of embodiment 10 or 11, further comprising at least one plant, plant part, or extract thereof comprising said at least one glucosinolate.
13. The bacterial strain composition of embodiment 12, wherein said extract comprises an extract from at least one cruciferous plant or plant part or wherein said at least one plant or plant part comprises at least one cruciferous plant or plant part.
14. The bacterial strain composition of embodiment 13, wherein said at least one cruciferous plant or plant part is selected from the group consisting of broccoli, cauliflower, and Brussels sprouts.
15. The bacterial strain composition of any one of embodiments 10-14, wherein an effective amount of said bacterial strain increases conversion of said at least one glucosinolate to isothiocyanate.
16. The bacterial strain composition of any one of embodiments 10-15, wherein said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof is present at about $10^6$ CFU/gram to about $10^{10}$ CFU/gram or at about $10^6$ CFU/ml to about $10^{10}$ CFU/ml.
17. The bacterial strain composition of embodiment 16, wherein said bacterial cell, spore, forespore, or combination of cells, forespores, and/or spores, or the active variant thereof is present at about $10^8$ CFU/gram to about $10^{10}$ CFU/gram or at about $10^8$ CFU/ml to about $10^{10}$ CFU/ml.
18. The bacterial strain composition of any one of embodiments 1-17, wherein said bacterial strain composition further comprises a carrier.
19. The bacterial strain composition of any one of embodiments 1-18, wherein said bacterial strain composition comprises a capsule, gel, paste, tablet, powder, or liquid.
20. The bacterial strain composition of any one of embodiments 1-19, wherein said composition comprises at least one additional bacterial strain.
21. The bacterial strain composition of embodiment 20, wherein the at least one additional bacterial strain is selected from the group consisting of a *Bacillus* spp, *Enterococcus* spp., *Bifidobacterium* spp., *Lactobacillus* spp., *Saccharomyces* spp., *Streptococcus* spp., *Propionibacterium* spp., Megasphaera spp., *Prevotella* spp., and *Pediococcus* spp.
22. The bacterial strain composition of any one of embodiments 1-21, further comprising at least one prebiotic.
23. A pharmaceutical composition comprising a bacterial strain comprising:
   (a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
   (b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof; and a pharmaceutically acceptable carrier that is not naturally-occurring with said bacterial cell, spore, or forespore.
24. The pharmaceutical composition of embodiment 23, further comprising at least one glucosinolate.
25. The pharmaceutical composition of embodiment 24, wherein said at least one glucosinolate comprises glucoraphanin.
26. The pharmaceutical composition of embodiment 24 or 25, wherein said composition comprises at least one plant, plant part or extract thereof comprising said at least one glucosinolate.
27. The pharmaceutical composition of embodiment 26, wherein said plant extract comprises an extract from at least one cruciferous plant or plant part or said at least one plant or plant part comprises a cruciferous plant or plant part.
28. The pharmaceutical composition of embodiment 27, wherein said at least one cruciferous plant or plant part is selected from the group consisting of broccoli, cauliflower, and Brussels sprouts.
29. The pharmaceutical composition of any one of embodiments 23-28, wherein said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof is present at about $10^6$ CFU/gram to about $10^{10}$ CFU/gram or at about $10^6$ CFU/ml to about $10^{10}$ CFU/ml.
30. The pharmaceutical composition of embodiment 29, wherein said bacterial cell, spore, forespore, or combination of cells, forespores, and/or spores, or the active variant thereof is present at about $10^8$ CFU/gram to about $10^{10}$ CFU/gram or at about $10^8$ CFU/ml to about $10^{10}$ CFU/ml.
31. The pharmaceutical composition of any one of embodiments 23-30, wherein said pharmaceutical composition comprises a capsule, gel, paste, tablet, powder, or liquid.
32. The pharmaceutical composition of any one of embodiments 23-31, wherein said composition comprises at least one additional bacterial strain.
33. The pharmaceutical composition of embodiment 32, wherein the at least one additional bacterial strain is selected from the group consisting of a *Bacillus* spp,

*Enterococcus* spp., *Bifidobacterium* spp., *Lactobacillus* spp., *Saccharomyces* spp., *Streptococcus* spp., *Propionibacterium* spp., Megasphaera spp., *Prevotella* spp., and *Pediococcus* spp.

34. The pharmaceutical composition of any one of embodiments 23-33, further comprising at least one prebiotic.

35. A method of increasing isothiocyanate production, said method comprising contacting at least one glucosinolate with an effective amount of a bacterial strain composition comprising:
(a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
(b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof.

36. The method of embodiment 35, wherein said at least one glucosinolate comprises glucoraphanin and said isothiocyanate comprises sulforaphane.

37. The method of embodiment 35 or 36, wherein said bacterial strain composition comprises a capsule, gel, paste, tablet, powder, or liquid.

38. The method of any one of embodiments 35-37, wherein said bacterial strain composition further comprises at least one additional bacterial strain.

39. The method of embodiment 38, wherein the additional bacterial strain is selected from the group consisting of a *Bacillus* spp, *Enterococcus* spp., *Bifidobacterium* spp., *Lactobacillus* spp., *Saccharomyces* spp., *Streptococcus* spp., *Propionibacterium* spp., Megasphaera spp., *Prevotella* spp., and *Pediococcus* spp.

40. The method of any one of embodiments 35-39, wherein said bacterial strain composition further comprises at least one prebiotic.

41. A method of increasing isothiocyanate production in a subject, said method comprising administering to a subject an effective amount of a bacterial strain composition comprising:
(a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
(b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof.

42. The method of embodiment 41, wherein said subject is administered at least one glucosinolate.

43. The method of embodiment 42, wherein said bacterial strain composition further comprises said at least one glucosinolate.

44. The method of embodiment 42 or 43, wherein said at least one glucosinolate comprises glucoraphanin and said isothiocyanate comprises sulforaphane.

45. The method of any one of embodiments 41-44, wherein said subject is administered at least one plant, plant part, or extract thereof comprising said at least one glucosinolate.

46. The method of embodiment 45, wherein said extract comprises an extract from at least one cruciferous plant or plant part or wherein said at least one plant or plant part comprises at least one cruciferous plant or plant part.

47. The method of embodiment 46, wherein said at least one cruciferous plant or plant part is selected from the group consisting of broccoli, cauliflower, and Brussels sprouts.

48. The method of any one of embodiments 41-47, wherein said subject is administered at least one additional bacterial strain.

49. The method of embodiment 48, wherein said bacterial strain composition further comprises said at least one additional bacterial strain.

50. The method of embodiment 48 or 49, wherein the at least one additional bacterial strain is selected from the group consisting of a *Bacillus* spp, *Enterococcus* spp., *Bifidobacterium* spp., *Lactobacillus* spp., *Saccharomyces* spp., *Streptococcus* spp., *Propionibacterium* spp., Megasphaera spp., *Prevotella* spp., and *Pediococcus* spp.

51. The method of any one of embodiments 41-50, wherein said subject is administered at least one prebiotic.

52. The method of embodiment 51, wherein said bacterial strain composition further comprises said at least one prebiotic.

53. The method of any one of embodiments 35-52, wherein said effective amount of said bacterial composition comprises about $10^6$ CFU/gram to about $10^{10}$ CFU/gram or about $10^6$ CFU/ml to about $10^{10}$ CFU/ml of said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof.

54. The method of embodiment 53, wherein said effective amount of said bacterial composition comprises about $10^8$ CFU/gram to about $10^{10}$ CFU/gram or about $10^8$ CFU/ml to about $10^{10}$ CFU/ml of said bacterial cell, spore, forespore, or combination of cells, forespores, and/or spores, or the active variant thereof.

55. The method of any one of embodiments 35-54, wherein said bacterial strain composition further comprises a carrier.

56. A method for treating an inflammatory disorder or a cancer in a subject, said method comprising administering to said subject an effective amount of a pharmaceutical composition comprising a pharmaceutically acceptable carrier and a bacterial strain comprising:
(a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
(b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof.

57. The method of embodiment 56, wherein said subject is administered at least one glucosinolate.

58. The method of embodiment 57, wherein said pharmaceutical composition further comprises said at least one glucosinolate.

59. The method of embodiment 57 or 58, wherein said at least one glucosinolate comprises glucoraphanin.

60. The method of any one of embodiments 57-59, wherein said subject is administered at least one plant, plant part, or extract thereof comprising said at least one glucosinolate.
61. The method of embodiment 60, wherein said extract comprises an extract from at least one cruciferous plant or plant part or wherein said at least one plant or plant part comprises at least one cruciferous plant or plant part.
62. The method of embodiment 61, wherein said at least one cruciferous plant or plant part is selected from the group consisting of broccoli, cauliflower, and Brussels sprouts.
63. The method of any one of embodiments 56-62, wherein said subject is administered at least one additional bacterial strain.
64. The method of embodiment 63, wherein said pharmaceutical composition further comprises said at least one additional bacterial strain.
65. The method of embodiment 63 or 64, wherein the at least one additional bacterial strain is selected from the group consisting of a *Bacillus* spp, *Enterococcus* spp., *Bifidobacterium* spp., *Lactobacillus* spp., *Saccharomyces* spp., *Streptococcus* spp., *Propionibacterium* spp., *Megasphaera* spp., *Prevotella* spp., and *Pediococcus* spp.
66. The method of any one of embodiments 56-65, wherein said subject is administered at least one prebiotic.
67. The method of embodiment 66, wherein said pharmaceutical composition further comprises said at least one prebiotic.
68. The method of any one of embodiments 56-67, wherein said effective amount comprises about $10^6$ CFU/gram to about $10^{10}$ CFU/gram or about $10^6$ CFU/ml to about $10^{10}$ CFU/ml of said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof.
69. The method of embodiment 68, wherein said effective amount comprises about $10^8$ CFU/gram to about $10^{10}$ CFU/gram or about $10^8$ CFU/ml to about $10^{10}$ CFU/ml of said bacterial cell, spore, forespore, or combination of cells, forespores, and/or spores, or the active variant thereof.
70. The method of any one of embodiments 56-69, wherein said pharmaceutical composition comprises a capsule, gel, paste, tablet, powder, or liquid.
71. The method of any one of embodiments 56-70, wherein said pharmaceutical composition is administered orally.
72. A method of increasing expression of a gene regulated by Nrf2, said method comprising contacting a cell with an effective amount of a bacterial strain composition comprising at least one glucosinolate and:
(a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
(b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof.
73. The method of embodiment 72, wherein said at least one glucosinolate comprises glucoraphanin and said isothiocyanate comprises sulforaphane.
74. The method of embodiment 72 or 73, wherein said bacterial strain composition further comprises at least one prebiotic.
75. The method of any one of embodiments 72-74, wherein said effective amount of said bacterial composition comprises about $10^6$ CFU/gram to about $10^{10}$ CFU/gram or about $10^6$ CFU/ml to about $10^{10}$ CFU/ml of said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof.
76. The method of embodiment 75, wherein said effective amount of said bacterial composition comprises about $10^8$ CFU/gram to about $10^{10}$ CFU/gram or about $10^8$ CFU/ml to about $10^{10}$ CFU/ml of said bacterial cell, spore, forespore, or combination of cells, forespores, and/or spores, or the active variant thereof.
77. The method of any one of embodiments 72-76, wherein said bacterial strain composition further comprises a carrier.
78. The method of any one of embodiments 72-77, wherein said cell comprises a liver cell, intestinal cell, kidney cell, lung cell, skin cell, or adipose cell.
79. The method of any one of embodiments 72-78, wherein said gene comprises an antioxidant response element in its regulatory region.
80. Use of the bacterial strain composition of any one of embodiments 1-22 or the pharmaceutical composition of any one of embodiments 23-34 for the treatment of an inflammatory disorder or a cancer in a subject.
81. Use of the bacterial strain composition of any one of embodiments 1-22 or the pharmaceutical composition of any one of embodiments 23-34 for the manufacture of a medicament useful for treating an inflammatory disorder or a cancer in a subject.

DETAILED DESCRIPTION

Figure 1:
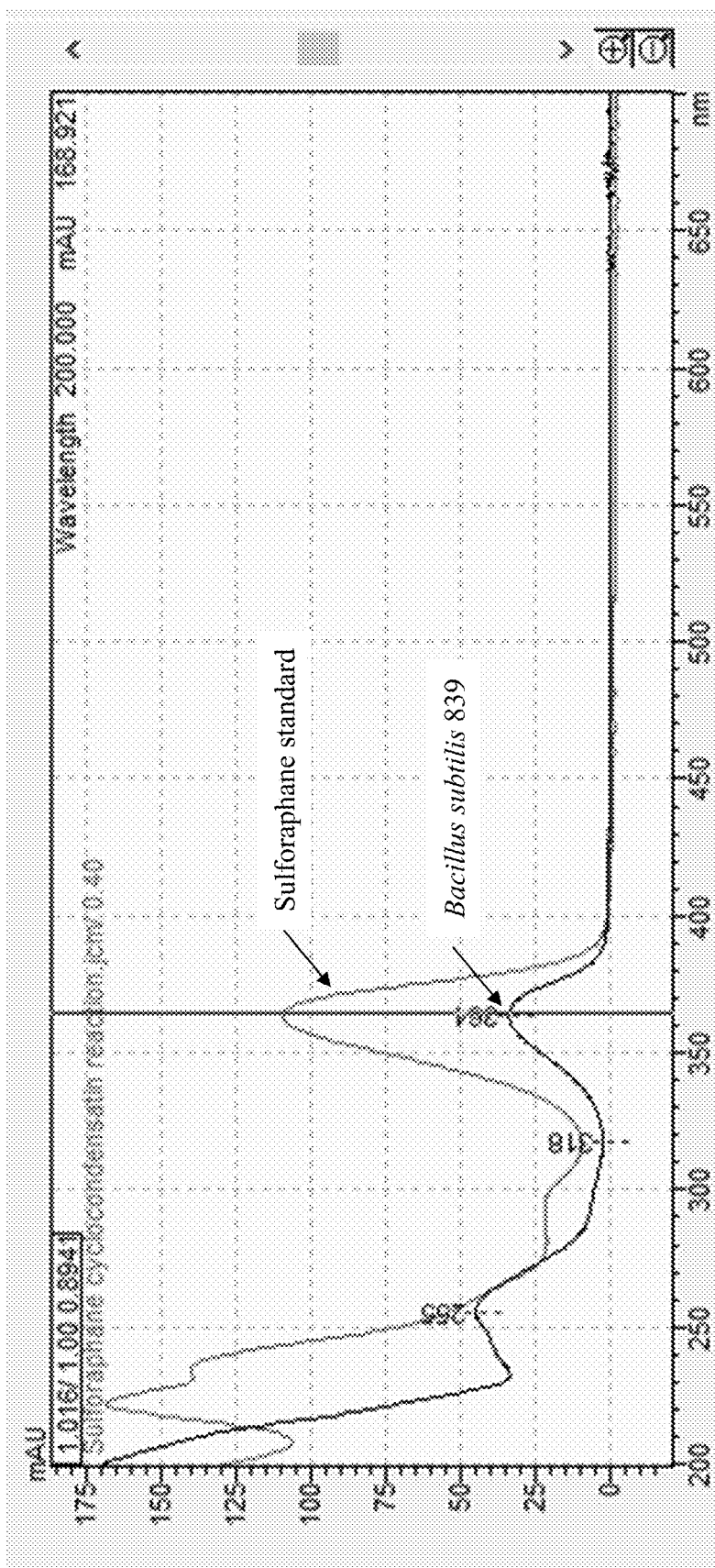
FIG. 1 shows a sulforaphane cyclocondensation reaction ultra violet spectrum. The ultra violet spectrum of minimal media after 24 hours with *Bacillus subtilis* 839 in the presence of glucoraphanin directly correlates with the ultra violet spectrum of the sulforaphane standard after cyclocondensation.

The present disclosure now will be described more fully hereinafter. The disclosure may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural references unless the context clearly dictates otherwise.

I. Overview

Provided herein are a strain of *Bacillus subtilis* (i.e., *Bacillus subtilis* 839), a strain of *Bacillus subtilis* (i.e., *Bacillus subtilis* CO4_4), and two strains of *Pediococcus pentosaceous* (i.e., *Pediococcus pentosaceous* M3_H01 and *Pediococcus pentosaceous* M2_H12), each of which expresses a myrosinase gene capable of producing a functional myrosinase enzyme.

The production of isothiocyanates (e.g., sulforaphane) naturally occurs from the controlled breakdown of glucosinolates found in cruciferous plants. In the plant cell, glucosinolates and the myrosinase enzyme are located in separate compartments and interact only after disruption of the cells, such as through chewing or processing. Myrosinase is a heat labile enzyme and is therefore destroyed through cooking, steaming or processing, rendering it inactive. The majority of broccoli and many other cruciferous plants are eaten cooked or from frozen storage; therefore, most myrosinase activity is destroyed and the level of isothiocyanates (e.g., sulforaphane) is negligible.

The identification of bacterial strains that have an active myosinase gene and enzyme allows for the use of a probiotic that is capable of surviving in the gastrointestinal tract to produce isothyocyanates in the intestine by biotransforming glucosinolates (e.g., glucoraphanin) that can be ingested through a diet consisting of broccoli, cauliflower, Brussels sprouts, or other members of the cruciferous plant family or the administration of an extract of such plants. This approach allows for the capture of isothiocyanates (e.g., sulforaphane) from cooked, processed, or frozen vegetables. The isothiocyanates can then be absorbed into the body immediately after production.

The bacterial strains described herein (and in some embodiments, a cruciferous plant, plant part or extract thereof) can be administered orally as a dietary supplement in a powder, capsule, gel, paste, or tablet and in combinations with food items or alone, in oils, as a suppository, in lubricants, sachets, topically along with at least one glucosinolate in a matrix, or via other administration routes.

As used herein, "myrosinase" refers to a β-thioglucoside glucohydrolase enzyme (EC 3.2.1.147) capable of cleaving, in the presence of water, the β-thioglucoside linkage within a glucosinolate, releasing D-glucose. The resulting aglycone undergoes a spontaneous Lossen-like rearrangement, releasing a sulfate. The last step in the mechanism is subject to the greatest variety depending on the physiological conditions under which the reaction takes place and can result in the formation of an isothiocyanate, thiocyanate, or nitrile. At neutral pH, the primary product is the isothiocyanate. Under acidic conditions (pH<3), and in the presence of ferrous ions or epithiospecifer proteins, the formation of nitriles is favored instead.

Myrosinase exists as a dimer with subunits of 60-70 kDa each linked by a zinc atom (Burmeister et al. (1997) *Structure* 5(5):663-676, which is incorporated herein in its entirety). Myrosinase enzyme sequences are known in the art and a non-limiting example of a myrosinase enzyme is the *Lactobacillus plantarum* subsp. *plantarum* myrosinase enzyme, the nucleotide and amino acid sequence of which is set forth as SEQ ID NOs: 9 and 10, respectively.

As used herein, "a glucosinolate" refers to a β-thioglucoside N-hydroxysulfate with a side chain and a sulfur-linked β-D-glucopyranose moiety. Every glucosinolate contains a central carbon atom, which is bound via a sulfur atom to the thioglucose group and via a nitrogen atom to a sulfate group (making a sulfated aldoxime). In addition, the central carbon is bound to a side group. Different glucosinolates have different side groups. Glucosinolates have the ability to convert into an isothiocyanate upon hydrolysis of the thioglucoside bond by the enzyme myrosinase. Glucosinolates can be categorized in the following classes: aliphatic, omega-methylthioalkyl, aromatic and heterocyclic (i.e., indole). Glucoraphanin is classified as an aliphatic monoheterocyclic compound.

In some embodiments, compositions and methods further comprise the provision of glucosinolates that can be acted upon by the myrosinase of the presently disclosed bacterial strains. In some of these embodiments, the glucosinolate is a naturally-occurring glucosinolate, for example, within a plant. Non-limiting examples of naturally-occurring glucosinolates include glucoraphanin, sinigrin, progoitrin, and gluconasturtiin. In other embodiments, the provided glucosinolate is not naturally-occurring.

Non-limiting glucosinolates that can be used in the presently disclosed compositions and methods include 3-Methyoxycarbonylpropyl, 1-Acetyl-indol-3-ylmethyl, 4-(4'-O-Acetyl-α-L-rhamnopyranosyloxy)benzyl, 2-(α-L-Arabinopryanosyloxy)-2-phenyl ethyl, 4-(Benzoyloxy) butyl, 2-(Benzoyloxy)ethyl, 2-Benzoyloxy-1-ethylethyl, Benzoyloxymethyl, 2-Benzyoloxy-1-methylethyl, 3-(Benzoyloxy)propyl, Benzyl, 3-Butenyl, n-Butyl, 3,4-Dihydroxybenzyl, 3,4-Dimethoxybenzyl, Etyl, 1-Ethyl-2-hydroxyethyl, 6-Heptenyl, 5-Hexenyl, n-Hexyl, 2-Hydroxybenzyl, 3-Hydroxybenzyl, 4-Hydroxybenzyl, 2(R)-2-Hydroxy-3-butenyl, 2(S)-2-Hydroxy-3-butenyl, 3-Hydroxybutyl, 4-Hydroxybutyl, 2-Hydroxyethyl, 4-Hydroxyindol-3-ylmethyl, 2-Hydroxyl-2-methylbutyl, 1-(Hydroxymethyl)propyl, 2-Hydroxy-2-methylpropyl, 3-Hydroxy-6-(methylsufinyl)hexyl, 3-Hydroxy-5-(methylsufinyl)pentyl, 3-Hydroxy-6-(methylsulfonyl)hexyl, 3-Hydroxy-5-(methylsulfonyl)pentyl, 3-Hydroxy-6-(methylthio)hexyl, 3-Hydroxy-5-(methylthio)pentyl, 2-Hydroxyl-4-pentenyl, 2-Hydroxypentyl, 2(R)-Hydroxy-2-phenylethyl, 2-Hydroxypropyl, 3-Hydroxypropyl, Indol-3-ylmethyl, 2-Methoxybenzyl, 3-Methoxybenzyl, 4-Methoxybenzyl, 1-Methoxyindol-3-ylmethyl, 4-Methoxyindol-3-ylmethyl, 2-(4-Methoxyphenyl)-2,2-dimethylethyl, 2-(4-Methoxyphenyl)-2-hydroxyethyl, Methyl, 3-Methyl-3-butenyl, 1-Methylbutyl, 2-Methylbutyl, 3-Methylbutyl, 1-Methylethyl, 1-Methyl-2-hydroxyethyl, 3-Methylpentyl, 4-Methylpentyl, 2-Methyl-2-propenyl, 1-Methylpropyl, 2-Methylpropyl, 4-Methylsulfinyl-3-butenyl, 4-(Methyl sulfinyl)butyl, 10-(Methyl sulfinyl)decyl, 7-(Methyl sulfinyl)heptyl, 6-(Methyl sulfinyl)hexyl, 9-(Methyl sulfinyl)nonyl, 8-(Methyl sulfinyl) octyl, 7-Methylsufinyl-3-oxoheptyl, 8-Methylsulfinyl-3-oxooctyl, 5-(Methylsulfinyl)pentyl, 3-(Methyl sulfinyl)propyl, 11-(Methylsulfinyl)undecyl, 4-Methylsulfynol-3-butenyl, 4-(Methyl sulfonyl)butyl, 10-(Methyl sulfonyl) decyl, 6-(Methyl sulfonyl)hexyl, 9-(Methylfsulfonyl)nonyl, 8-(Methylsulfonyl)octyl, 5-(Methylsulfonyl)pentyl, 3-(Methyl sulfonyl)propyl, 4-Methylthio-3-butenyl, 4-(Metylthio)butyl, 10-(Methylthio)decyl, 2-(Methylthio) ethyl, 7-(Methylyhio)heptl, 6-(Methylthio)hexyl, 9-(Methylthio)nonyl, 7-Methylthio-3-oxoheptyl, 6-Methylthio-3-oxohexyl, 8-(Methylthio)octyl, 8-Methylthio-3-oxooctyl, 5-(Methylthio)pentyl, 3-(Methylthio)propyl, 4-Oxoheptyl, 5-Oxoheptyl, 5-Oxooctyl, 4-Oxopentyl, 1-Pentenyl, 4-Pentenyl, n-Pentyl, Phenyl, 4-Phenylbutyl, 2-Phenylethyl, 3-Phenylpropyl, 2-Propenyl, n-Propyl, 2-(α-L-Rhamnopyranosyloxy)benzyl, 4-(α-L-Rhamnopyranosyloxy)benzyl, 6-Sinapoyl-β-D-1-thioglucoside of 4-methylsulfinylbut-3-enyl, 1-Sulfo-indol-3-ylmethyl, 4,5,6,7-Tetrahydroxydecyl, 3,4,5-Trimethixybenzyl, "iso"-Heptyl, "iso"-Hexyl, 5-(Benzoyloxy)pentyl, 6-(Benzoyloxy)hexyl, 2-O-Apiosylglucomatronalin, and 3-O-Apiosylglucomatronalin 3,4-dimethoxybenzoyl ester. Other non-limiting examples of glucosinolates include allylglucosinolate (sinigrin), the precursor of allyl isothiocyanate; benzylgiucosinolate (giucotropaeolin), the precursor of benzyl isothiocyanate; phenethylglucosinolate (gluconasturtiin), the precursor of phenethyl isothiocyanate; and (R)-4-(methylsulfinyl)butylglucosinotate (glucoraphanin), the precursor of (R)-4-(methylsulfinyl)butyl isothiocyanate (sulforaphane).

As used herein, "glucoraphanin" refers to the glucosinolate precursor to sulforaphane. Glucoraphanin is also known as sulforaphane glucosinolate, 4-methylsulfinylbutyl glucosinolate and 1-S-[(1E)-5-(methylsulfinyl)-N-(sulfonatooxy) pentanimidoyl]-1-thio-β-D-glucopyranose.

As used herein, "isothiocyanate" refers to a chemical compound with the structure R—N=C=S, where R is an alkyl or aryl group. Non-limiting examples of isothiocyanates that can be produced by the myrosinase enzyme of the presently disclosed bacterial strains acting upon a glucosinolate include sulforaphane, allyl isothiocyanate, phenethyl isothiocyanate, phenyl isothiocyanate, and benzyl isothiocyanate.

As used herein, "sulforaphane" refers to the isothiocyanate 1-isothiocyanato-4-methyl sulfinylbutane.

Though not wishing to be bound by any particular theory, it is believed that isothiocyanates (e.g., sulfurophane) may provide protection against oxidative and inflammatory stress, such as disturbances of systems that protect cells against oxidative damage, heat shock, and disturbances caused by protein misfolding. These protective mechanisms are thought to be at least partly mediated by the transcription factor Nrf2 which controls expression of genes of the human genome via the Keap1/Nrf2/ARE regulatory system. This system may be upregulated in many tissues by isothiocyanates (e.g., sulforaphane), which bind directly to the NF-E2 p45-related factor 2 (Nrf2) negative regulator Kelch-like ECH associated protein 1 (Keap1), stabilizing the Nrf2 transcription factor, which enhances the expression of nearly 500 genes encoding drug-metabolizing, antioxidant, and anti-inflammatory proteins, including those with an antioxidant response element (ARE) in their promoter regions, such as phase II enzymes (See, e.g., Baird et al. (2011) *Archives of Toxicology* 85:241-272; and Baird et al. (2014) *Biotechnology Advances* 32(6):1133-1144; each of which is incorporated in its entirety by this reference). Isothiocyanates also inhibit members of the cytochrome P-450 family, including CYP1A1, 1A2, 2B1/2, 2E1, and 3A4. In addition, isothiocyanates have inhibitory effects on the growth of various types of cancer cells and can induce apoptosis of cancer cells. Isothyiocyanates also function as histone deacetylase inhibitors. See, for example, Wu et al. (2009) *Acta Pharmacol Sin.* 30(5):501-512.

The presently disclosed bacterial strains can be used as probiotics. The term "probiotics" has been defined by the Food and Agriculture Organization of the United Nations (FAO) and World Health Organization (WHO) as live microorganisms which when administered in adequate amounts confer a health benefit on the host. Probiotics include beneficial bacteria that when consumed or otherwise administered to the gastrointestinal tract improve the health of the subject. In some embodiments, the beneficial bacteria colonize the gut, allowing for a more persistent beneficial effect.

II. Bacterial Strains

Various bacterial strains are provided which can be used to convert at least one glucosinolate to an isothyocyanate. Such bacterial strains include the *Bacillus subtilis* strain 839, *Bacillus subtilis* strain CO4_4, *Pediococcus pentosaceus* strain M3_H01, and *Pediococcus pentosaceus* strain M2_H12, or an active variant of any thereof. Cell populations comprising one or more of *Bacillus subtilis* strain 839, *Bacillus subtilis* strain CO4_4, *Pediococcus pentosaceus* strain M3_H01, and *Pediococcus pentosaceus* strain M2_H12, or an active variant of any thereof are provided, as well as populations of spores derived from each of these strains, or any preparation thereof. Thus, various bacterial strains and/or compositions provided herein comprise as an active ingredient a cell population, spore, forespore, or combination thereof, of one or more of *Bacillus subtilis* strain 839, *Bacillus subtilis* strain CO4_4, *Pediococcus pentosaceus* strain M3_H01, and *Pediococcus pentosaceus* strain M2_H12, or an active variant of any thereof.

*Bacillus subtilis* strain 839 was deposited with the Patent Depository of the National Center for Agricultural Utilization Research *Agricultural Research* Service, U.S. Department of Agriculture, 1815 North University Street, Peoria, Ill. 61604 U.S.A. on Apr. 12, 2020 and assigned NRRL No. B-67951.

*Bacillus subtilis* strain CO4_4 was deposited with the Patent Depository of the National Center for Agricultural Utilization Research *Agricultural Research* Service, U.S. Department of Agriculture, 1815 North University Street, Peoria, Ill. 61604 U.S.A. on Jan. 14, 2021 and assigned NRRL No. B-68014.

*Pediococcus pentosaceus* strain M3_H01 was deposited with the Patent Depository of the National Center for Agricultural Utilization Research *Agricultural Research* Service, U.S. Department of Agriculture, 1815 North University Street, Peoria, Ill. 61604 U.S.A. on Jan. 14, 2021 and assigned NRRL No. B-68013.

*Pediococcus pentosaceus* strain M2_H12 was deposited with Patent Depository of the National Center for Agricultural Utilization Research *Agricultural Research* Service, U.S. Department of Agriculture, 1815 North University Street, Peoria, Ill. 61604 U.S.A. on Jan. 14, 2021 and assigned NRRL No. B-68012.

Each of the deposits identified above will be maintained under the terms of the Budapest Treaty on the International Recognition of the Deposit of Microorganisms for the Purposes of Patent Procedure. Each deposit was made merely as a convenience for those of skill in the art and is not an admission that a deposit is required under 35 U.S.C. § 112.

The term "isolated" encompasses a bacterium, spore, or other entity or substance, that has been (1) separated from at least some of the components with which it was associated when initially produced (whether in nature or in an experimental setting), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated.

As used herein, a substance is "pure" if it is substantially free of other components. The terms "purify," "purifying" and "purified" refer to a bacterium, spore, or other material that has been separated from at least some of the components with which it was associated either when initially produced or generated (e.g., whether in nature or in an experimental setting), or during any time after its initial production. A bacterium or spore or a bacterial population or a spore population may be considered purified if it is isolated at or after production, such as from a material or environment containing the bacterium or bacterial population or spore, and a purified bacterium or bacterial population or spore may contain other materials up to about 10%, about 20%, about 30%, about 40%, about 50%, about 60%, about 70%, about 80%, about 90%, or above about 90% and still be considered purified. In some embodiments, purified bacteria or spores and bacterial populations or spore populations are more than about 80%, about 85%, about 90%, about 91%, about 92%, about 93%, about 94%, about 95%, about 96%, about 97%, about 98%, about 99%, or more than about 99% pure. In specific embodiments, a culture of bacteria contains no other bacterial species in quantities to be detected by normal bacteriological techniques.

By "population" is intended a group or collection that comprises two or more (i.e., 10, 100, 1,000, 10,000, 1×10$^6$, 1×10$^7$, or 1×10$^8$ or greater), for example, of a given bacterial strain. Various compositions are provided herein that comprise a population of at least one bacterial strain or a mixed population of individuals from more than one bacterial strain. In specific embodiments, the population of at least one of a bacterial strain (i.e., cells of *Bacillus subtilis* 839, *Bacillus subtilis* CO4_4, *Pediococcus pentosaceus* M3_H01, or *Pediococcus pentosaceus* M2_H12, or an active variant of any thereof, or spores or forespores or a combination of cells, forespores and/or spores, formed from one or more of *Bacillus subtilis* 839, *Bacillus subtilis* CO4_4, *Pediococcus pentosaceus* M3_H01, and *Pediococcus pentosaceus* M2_H12, or an active variant of any thereof) comprises a concentration of at least about 10$^4$ CFU/ml to about 10$^{12}$ CFU/ml, about 10$^5$ CFU/ml to about 10$^{12}$ CFU/ml, about 10$^6$ CFU/ml to about 10$^{12}$ CFU/ml, about 10$^7$ CFU/ml to about 10$^{12}$ CFU/ml, about 10$^8$ CFU/ml to about 10$^{12}$ CFU/ml, about 10$^9$ CFU/ml to about 10$^{12}$ CFU/ml, about 10$^{10}$ CFU/ml to about 10$^{12}$ CFU/ml, about 10$^{11}$ CFU/ml to about 10$^{12}$ CFU/ml, about 10$^5$ CFU/ml to about 10$^{11}$ CFU/ml, about 10$^5$ CFU/ml to about 10$^{11}$ CFU/ml, about 10$^6$ CFU/ml to about 10$^{11}$ CFU/ml, about 10$^7$ CFU/ml to about 10$^{11}$ CFU/ml, about 10$^8$ CFU/ml to about 10$^{11}$ CFU/ml, about 10$^9$ CFU/ml to about 10$^{11}$ CFU/ml, about 10$^{10}$ CFU/ml to about 10$^{11}$ CFU/ml, about 10$^5$ CFU/ml to about 10$^{10}$ CFU/ml, about 10$^6$ CFU/ml to about 10$^{10}$ CFU/ml, about 10$^7$ CFU/ml to about 10$^{10}$ CFU/ml, about 10$^8$ CFU/ml to about 10$^{10}$ CFU/ml, or about 10$^9$ CFU/ml to about 10$^{10}$ CFU/ml. In other embodiments, the concentration of the bacterial strain provided herein or active variant thereof comprises or consists of at least about 10$^4$ CFU/ml, at least about 10$^5$ CFU/ml, at least about 10$^6$ CFU/ml, at least about 10$^7$ CFU/ml, at least about 10$^8$ CFU/ml, at least about 10$^9$ CFU/ml, at least about 10$^{10}$ CFU/ml, at least about 10$^{11}$ CFU/ml, or at least about 10$^{12}$ CFU/ml. In specific embodiments, the population of at least one of a bacterial strain (i.e., cells of *Bacillus subtilis* 839, *Bacillus subtilis* CO4_4, *Pediococcus pentosaceus* M3_H01, or *Pediococcus pentosaceus* M2_H12, or an active variant of any thereof, or spores or forespores or a combination of cells, forespores and/or spores, formed from one or more of *Bacillus subtilis* 839, *Bacillus subtilis* CO4_4, *Pediococcus pentosaceus* M3_H01, and *Pediococcus pentosaceus* M2_H12, or an active variant of any thereof) comprises a concentration of at least about 10$^4$ CFU/g to about 10$^{12}$ CFU/g, about 10$^5$ CFU/g to about 10$^{12}$ CFU/g, about 10$^6$ CFU/g to about 10$^{12}$ CFU/g, about 10$^7$ CFU/g to about 10$^{12}$ CFU/g, about 10$^8$ CFU/g to about 10$^{12}$ CFU/g, about 10$^9$ CFU/g to about 10$^{12}$ CFU/g, about 10$^{10}$ CFU/g to about 10$^{12}$ CFU/g, about 10$^{11}$ CFU/g to about 10$^{12}$ CFU/g, about 10$^5$ CFU/g to about 10$^{11}$ CFU/g, about 10$^5$ CFU/g to about 10$^{11}$ CFU/g, about 10$^6$ CFU/g to about 10$^{11}$ CFU/g, about 10$^7$ CFU/g to about 10$^{11}$ CFU/g, about 10$^8$ CFU/g to about 10$^{11}$ CFU/g, about 10$^9$ CFU/g to about 10$^{11}$ CFU/g, about 10$^{10}$ CFU/g to about 10$^{11}$ CFU/g, about 10$^5$ CFU/g to about 10$^{10}$ CFU/g, about 10$^6$ CFU/g to about 10$^{10}$ CFU/g, about 10$^7$ CFU/g to about 10$^{10}$ CFU/g, about 10$^8$ CFU/g to about 10$^{10}$ CFU/g, or about 10$^9$ CFU/g to about 10$^{10}$ CFU/g. In other embodiments, the concentration of the bacterial strain provided herein or active variant thereof comprises or consists of at least about 10$^4$ CFU/g, at least about 10$^5$ CFU/g, at least about 10$^6$ CFU/g, at least about 10$^7$ CFU/g, at least about 10$^8$ CFU/g, at least about 10$^9$ CFU/g, at least about 10$^{10}$ CFU/g, at least about 10$^{11}$ CFU/g, or at least about 10$^{12}$ CFU/g.

A "spore" refers to at least one dormant (at application) but viable reproductive unit of a bacterial species. Non-limiting methods by which spores are formed from each of *Bacillus subtilis* 839 and *Bacillus subtilis* CO4_4 (or variants of any thereof) are disclosed elsewhere herein. It is further recognized the populations disclosed herein can comprise a combination of vegetative cells and forespores (cells in an intermediate stage of spore formation); a combination of forespores and spores; or a combination of forespores, vegetative cells and/or spores. In specific embodiments, the *Bacillus subtilis* 839 or *Bacillus subtilis* CO4_4 (or variant of any thereof) is a viable cell, spore, or forespore.

A. Active Variants of a Bacterial Strain

Further provided are active variants of *Bacillus subtilis* 839, *Bacillus subtilis* CO4_4, *Pediococcus pentosaceus* M3_H01, and *Pediococcus pentosaceus* M2_H12. Active variants of the various bacterial strains provided herein include, for example, any isolate or mutant of *Bacillus subtilis* 839, *Bacillus subtilis* CO4_4, *Pediococcus pentosaceus* M3_H01, or *Pediococcus pentosaceus* M2_H12 that retains the ability to convert at least one glucosinolate (e.g., glucoraphanin) to an isothiocyanate (e.g., sulforaphone). An active variant includes a strain having all of the identifying characteristics of the recited strain. A "strain of the invention" includes active variants thereof.

By "modified bacterial strain" is intended a population wherein the strain has been modified (by selection and/or transformation) to have one or more additional traits of interest. Modified bacterial strains can be made through genetic engineering techniques and such engineered or recombinant bacterial strains grown to produce a modified population of bacterial strains. A recombinant bacterial strain can be produced by introducing polynucleotides into the bacterial host cell by transformation or by otherwise altering the native bacterial chromosome sequence, including but not limited to, gene editing approaches. Methods for transforming microorganisms are known and available in the art. See, generally, Hanahan, D. (1983) Studies on transformation of *Escherichia coli* with plasmids *J Mol. Biol.* 166, 557-77; Seidman, C. E. (1994) In: *Current Protocols in Molecular Biology*, Ausubel, F. M. et al. eds., John Wiley and Sons, NY; Choi et al. (2006) *J. Microbiol. Methods* 64:391-397; Wang et al. 2010.1 Chem. Technol. *Biotechnol.* 85:775-778. Transformation may occur by natural uptake of naked DNA by competent cells from their environment in the laboratory. Alternatively, cells can be made competent by exposure to divalent cations under cold conditions, by electroporation, by exposure to polyethyleneycol, by treatment with fibrous nanoparticles, or other methods well known in the art.

Active variants of the various bacteria provided herein can be identified by employing, for example, methods that determine the sequence identity relatedness between the 16S ribosomal RNA, methods to identify groups of derived and functionally identical or nearly identical strains include Multi-locus sequence typing (MLST), concatenated shared genes trees, Whole Genome Alignment (WGA), Average Nucleotide Identity, and MinHash (Mash) distance metric.

In one aspect, the active variants of *Bacillus subtilis* 839, *Bacillus subtilis* CO4_4, *Pediococcus pentosaceus* M3_H01, or *Pediococcus pentosaceus* M2_H12 include strains that are closely related to any of the disclosed strains by employing the Bishop MLST method of organism classification as defined in Bishop et al. (2009) *BMC Biology* 7(1)1741-7007-7-3. Thus, in specific embodiments, an active variant of a bacterial strain disclosed herein includes a bacterial strain that falls within at least a 80%, 85%, 86%, 87%, 88%, 89%, 90%, 91%, 92%, 93%. 94%, 95%, 96%, 97%, 98%, 98.5%, 98.8%, 99%, 99.1%, 99.2%, 99.3%, 99.4%, 99.5%, 99.6%, 99.7%, 99.8%, or 99.9% sequence cut off employing the Bishop method of organism classification as set forth in Bishop et al. (2009) *BMC Biology* 7(1)1741-7007-7-3, which is herein incorporated by reference in its entirety. Active variants of the bacteria identified by such methods will retain the ability to convert at least one glucosinolate (e.g., glucoraphanin) to an isothiocyanate (e.g., sulforaphone).

In some embodiments, the active variant of the bacterial strain(s) disclosed herein include strains that are closely related to any of the disclosed strains on the basis of the Average Nucleotide Identity (ANI) method of organism classification. ANI (see, for example, Konstantinidis, K. T., et al., (2005) *PNAS USA* 102(7):2567-72; and Richter, M., et al., (2009) *PNAS* 106(45):19126-31) and variants (see, for example, Varghese, N.J., et al., *Nucleic Acids Research* (Jul. 6, 2015): gkv657) are based on summarizing the average nucleotides shared between the genomes of strains that align in WGAs. Thus, in specific embodiments, an active variant of bacterial strain *Bacillus subtilis* 839, *Bacillus subtilis* CO4_4, *Pediococcus pentosaceus* M3_H01, and *Pediococcus pentosaceus* M2_H12 disclosed herein includes a bacterial strain that falls within at least a 90%, 95%, 96%, 97%, 97.5%, 98%, 98.5%, 98.8%, 99%, 99.5%, or 99.8% sequence cut off employing the ANI method of organism classification as set forth in Konstantinidis, K. T., et al., (2005) *PNAS USA* 102(7):2567-72, which is herein incorporated by reference in its entirety. Active variants of the bacteria identified by such methods will retain the ability to convert at least one glucosinolate (e.g., glucoraphanin) to an isothiocyanate (e.g., sulforaphone).

In particular embodiments, the active variants of the isolated bacterial strain(s) disclosed herein include strain(s) that are closely related to *Bacillus subtilis* 839, *Bacillus subtilis* CO4_4, *Pediococcus pentosaceus* M3_H01, or *Pediococcus pentosaceus* M2_H12 on the basis of 16S rDNA sequence identity. See Stackebrandt E, et al., "Report of the ad hoc committee for the re-evaluation of the species definition in bacteriology," *Int J Syst Evol Microbiol.* 52(3): 1043-7 (2002) regarding use of 16S rDNA sequence identity for determining relatedness in bacteria. In an embodiment, the active variant is at least 95% identical to any of the above strains on the basis of 16S rDNA sequence identity, at least 96% identical to any of the above strains on the basis of 16S rDNA sequence identity, at least 97% identical to any of the above strains on the basis of 16S rDNA sequence identity, at least 98% to any of the above strains on the basis of 16S rDNA sequence identity, at least 98.5% identical to any of the above strains on the basis of 16S rDNA sequence identity, at least 99% identical to any of the above strains on the basis of 16S rDNA sequence identity, at least 99.5% to any of the above strains on the basis of 16S rDNA sequence identity or at least 100% to any of the above strains on the basis of 16S rDNA sequence identity. Active variants of the bacteria identified by such methods will retain the ability to convert at least one glucosinolate (e.g., glucoraphanin) to an isothiocyanate (e.g., sulforaphone).

The MinHash (Mash) distance metric is a comparison method that defines thresholds for hierarchical classification of microorganisms at high resolution and requires few parameters and steps (Ondov et al. (2016) *Genome Biology* 17:132). The Mash distance estimates the mutation rate between two sequences directly from their MinHash sketches (Ondov et al. (2016) *Genome Biology* 17:132). Mash distance strongly corresponds to Average Nucleotide Identity method (ANI) for hierarchical classification (See, Konstantinidis, K. T. et al. (2005) *PNAS USA* 102(7):2567-72, herein incorporated by reference in its entirety). That is, an ANI of 97% is approximately equal to a Mash distance of 0.03, such that values put forth as useful classification thresholds in the ANI literature can be directly applied with the Mash distance.

Active variants of the bacterial strain(s) disclosed herein include strains that are closely related to *Bacillus subtilis* 839, *Bacillus subtilis* CO4_4, *Pediococcus pentosaceus* M3_H01, or *Pediococcus pentosaceus* M2_H12 on the basis of the Minhash (Mash) distance between complete genome DNA sequences. Thus, in specific embodiments, an active variant of a bacterial strain disclosed herein includes bacterial strains having a genome within a Mash distance of less than about 0.015 to the disclosed strains. In other embodiments, an active variant of a bacterial strain disclosed herein includes a distance metric of less than about 0.001, 0.0025, 0.005, 0.010, 0.015, 0.020, 0.025, or 0.030. A genome, as it relates to the Mash distance includes both bacterial chromosomal DNA and bacterial plasmid DNA. In other embodiments, the active variant of a bacterial strain has a genome that is above a Mash distance threshold to the disclosed strains that is greater than dissimilarity caused by technical variance. In further instances, the active variant of a bacterial strain has a genome that is above a Mash distance threshold to the disclosed strains that is greater than dissimilarity caused by technical variance and has a Mash distance of less than about 0.015. In other instances, the active variant of a bacterial strain has a genome that is above a Mash distance threshold to the disclosed strains that is greater than dissimilarity caused by technical variance and has a Mash distance of less than about 0.001, 0.0025, 0.005, 0.010, 0.015, 0.020, 0.025, or 0.030.

As used herein, "above technical variation" means above the Mash distance between two strains caused by errors in the genome assemblies provided the genomes being compared were each DNA sequenced with at least 20× coverage with the Illumina HiSeq 2500 DNA sequencing technology and the genomes are at least 99% complete with evidence for contamination of less than 2%. While 20× coverage is an art recognized term, for clarity, an example of 20× coverage is as follows: for a genome size of 5 megabases (MB), 100 MB of DNA sequencing from the given genome is required to have 20× sequencing coverage on average at each position along the genome. There are many suitable collections of marker genes to use for genome completeness calculations including the sets found in Campbell et al. (2013) *PNAS USA* 110(14):5540-45, Dupont et al. (2012) *ISMEJ* 6:1625-1628, and the CheckM framework (Parks et al. (2015) *Genome Research* 25:1043-1055); each of these references is herein incorporated in their entirety. Contamination is defined as the percentage of typically single copy marker genes that are found in multiple copies in the given genome sequence (e.g. Parks et al. (2015) *Genome Research* 25:1043-1055); each of these references is herein incorporated in their entirety. Completeness and contamination are calculated using the same collection of marker genes. Unless otherwise stated, the set of collection markers employed in the completeness and contamination assay is those set forth in Campbell et al. (2013) *PNAS USA* 110(14):5540-45, herein incorporated by reference.

Exemplary steps to obtain a distance estimate between the genomes in question are as follows: (1) Genomes of sufficient quality for comparison must be produced. A genome of sufficient quality is defined as a genome assembly created with enough DNA sequence to amount to at least 20× genome coverage using Illumina HiSeq 2500 technology. The genome must be at least 99% complete with contamination of less than 2% to be compared to the claimed microbe's genome. (2) Genomes are to be compared using the Minhash workflow as demonstrated in Ondov et al. (2016) *Genome Biology* 17:132, herein incorporated by reference in its entirety. Unless otherwise stated, parameters employed are as follows: "sketch" size of 1000, and "k-mer length" of 21. (3) Confirm that the Mash distance between the two genomes is less than 0.001, 0.0025, 0.005, 0.010, 0.015, 0.020, 0.025, or 0.030. Using the parameters and methods stated above, a Mash distance of 0.015 between two genomes means the expected mutation rate is 0.015 mutations per homologous position. Active variants of the bacteria identified by such methods will retain the ability to convert at least one glucosinolate (e.g., glucoraphanin) to an isothiocyanate (e.g., sulforaphane).

B. Methods of Cultivating Bacterial Strains

Populations or cultures of *Bacillus subtilis* 839, *Bacillus subtilis* CO4_4, *Pediococcus pentosaceus* M3_H01, or *Pediococcus pentosaceus* M2_H12 can be produced by cultivation of the bacterial strain. Cultivation can be started by scaling-up a seed culture. This involves repeatedly and aseptically transferring the culture to a larger and larger volume to serve as the inoculum for the fermentation, which can be carried out in large stainless steel fermentors in medium containing proteins, carbohydrates, and minerals necessary for optimal growth of the strain. Non-limiting exemplary media is Tryptic Soy Broth (TSB) for the *Bacillus* strains or MRS (de Man, Rogosa, and Sharpe (1960) *J Appl. Bacteriol.* 23:130, which is herein incorporated by reference in its entirety) for the *Pediococcus* strains. After the bacterial inoculum is added to the fermentation vessel, the temperature and agitation are controlled to allow maximum growth. Once the culture reaches a maximum population density, the culture is harvested by separating the cells from the fermentation medium. This separation is commonly performed by centrifugation.

The concentration of the bacterial culture can be measured from any sample of fermentation broth or bacterial strain composition. A colony forming unit (CFU) is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit can be a more useful unit measurement than cell number.

The various compositions and formulations disclosed herein can comprise an amount of at least one of a bacterial strain (i.e., cells of *Bacillus subtilis* 839, *Bacillus subtilis* CO4_4, *Pediococcus pentosaceus* M3_H01, or *Pediococcus pentosaceus* M2_H12, or an active variant of any thereof, or spores or forespores or a combination of cells, forespores and/or spores, formed from one or more of *Bacillus subtilis* 839, *Bacillus subtilis* CO4_4, *Pediococcus pentosaceus* M3_H01, and *Pediococcus pentosaceus* M2_H12, or an active variant of any thereof). Such an amount can comprise a concentration of at least one bacterial strain of at least about $10^4$ CFU/g to about $10^{12}$ CFU/g, about $10^5$ CFU/g to about $10^{12}$ CFU/g, about $10^6$ CFU/g to about $10^{12}$ CFU/g, about $10^7$ CFU/g to about $10^{12}$ CFU/g, about $10^8$ CFU/g to about $10^{12}$ CFU/g, about $10^9$ CFU/g to about $10^{12}$ CFU/g, about $10^{10}$ CFU/g to about $10^{12}$ CFU/g, about $10^{11}$ CFU/g to about $10^{12}$ CFU/g, about $10^5$ CFU/g to about $10^{11}$ CFU/g, about $10^5$ CFU/g to about $10^{11}$ CFU/g, about $10^6$ CFU/g to about $10^{11}$ CFU/g, about $10^7$ CFU/g to about $10^{11}$ CFU/g, about $10^8$ CFU/g to about $10^{11}$ CFU/g, about $10^9$ CFU/g to about $10^{11}$ CFU/g, about $10^{10}$ CFU/g to about $10^{11}$ CFU/g, about $10^5$ CFU/g to about $10^{10}$ CFU/g, about $10^6$ CFU/g to about $10^{10}$ CFU/g, about $10^7$ CFU/g to about $10^{10}$ CFU/g, about $10^8$ CFU/g to about $10^{10}$ CFU/g, or about $10^9$ CFU/g to about $10^{10}$ CFU/g. In other embodiments, the concentration of at least one of the bacterial strains provided herein or active variant thereof comprises or consists of at least about $10^4$ CFU/g, at least about $10^5$ CFU/g, at least about $10^6$ CFU/g, at least about $10^7$ CFU/g, at least about $10^8$ CFU/g, at least about $10^9$ CFU/g, at least about $10^{10}$ CFU/g, at least about $10^{11}$ CFU/g, or at least about $10^{12}$ CFU/g. Another such an amount can comprise a concentration of at least one bacterial strain of at least about $10^4$ CFU/ml to about $10^{12}$ CFU/ml, about $10^5$ CFU/ml to about $10^{12}$ CFU/ml, about $10^6$ CFU/ml to about $10^{12}$ CFU/ml, about $10^7$ CFU/ml to about $10^{12}$ CFU/ml, about $10^8$ CFU/ml to about $10^{12}$ CFU/ml, about $10^9$ CFU/ml to about $10^{12}$ CFU/ml, about $10^{10}$ CFU/ml to about $10^{12}$ CFU/ml, about $10^{11}$ CFU/ml to about $10^{12}$ CFU/ml, about $10^5$ CFU/ml to about $10^{11}$ CFU/ml, about $10^5$ CFU/ml to about $10^{11}$ CFU/ml, about $10^6$ CFU/ml to about $10^{11}$ CFU/ml, about $10^7$ CFU/ml to about $10^{11}$ CFU/ml, about $10^8$ CFU/ml to about $10^{11}$ CFU/ml, about $10^9$ CFU/ml to about $10^{11}$ CFU/ml, about $10^{10}$ CFU/ml to about $10^{11}$ CFU/ml, about $10^5$ CFU/ml to about $10^{10}$ CFU/ml, about $10^6$ CFU/ml to about $10^{10}$ CFU/ml, about $10^7$ CFU/ml to about $10^{10}$ CFU/ml, about $10^8$ CFU/ml to about $10^{10}$ CFU/ml, or about $10^9$ CFU/ml to about $10^{10}$ CFU/ml. In other embodiments, the concentration of at least one of the bacterial strains provided herein or active variant thereof comprises or consists of at least about $10^4$ CFU/ml, at least about $10^5$ CFU/ml, at least about $10^6$ CFU/ml, at least about $10^7$ CFU/ml, at least about $10^8$ CFU/ml, at least about $10^9$ CFU/ml, at least about $10^{10}$ CFU/ml, at least about $10^{11}$ CFU/ml, or at least about $10^{12}$ CFU/ml.

C. Formulations of Bacterial Strains

The bacterial strains provided herein (i.e., cells of *Bacillus subtilis* 839, *Bacillus subtilis* CO4_4, *Pediococcus pentosaceus* M3_H01, or *Pediococcus pentosaceus* M2_H12, or an active variant of any thereof, or spores or forespores or a combination of cells, forespores and/or spores, formed from one or more of *Bacillus subtilis* 839, *Bacillus subtilis* CO4_4, *Pediococcus pentosaceus* M3_H01, and *Pediococcus pentosaceus* M2_H12, or an active variant of any thereof) can be formulated as a paste (e.g., cell paste), a powder, a capsule, a tablet, a granule, a cell pellet, dust, a slurry, aqueous or oil based liquid products, gel, and the like.

Common bacterial strain compositions, such as probiotic preparations, are liquid solutions and concentrates or lyophilized powders for resuspension, which can be enclosed in a capsule, vial, or pouch. Such formulations will comprise the bacterial strains provided herein or an active variant thereof, in addition to carriers and other agents. As used herein, the term "carrier" refers to an inert compound that is compatible with any other ingredients in the formulation and is not deleterious to the active compound (i.e., bacterial strains) or a subject that the formulation is administered thereto. Suitable carriers can be added to improve recovery, efficacy, or physical properties and/or to aid in packaging and administration. Such carriers may be added individually or in combination. Non-limiting examples of carriers include proteins, carbohydrates, fats, enzymes, vitamins, immune modulators, oligosaccharides, milk replacers, minerals, amino acids, coccidiostats, acid-based products, medicines (such as antibiotics), other probiotics, and/or prebiotics. Common carriers include cellulose, sugar, glucose, lactose, whey powder, or rice hulls The carrier(s) may comprise about 30% weight per weight, weight per volume, or volume per volume, of the final composition. In some embodiments, the carrier(s) may comprise about 40%, about 50%, about 60%, about 70%, about 80%, about 90%, about 91%, about 92%, about 93%, about 94%, about 95%, about 96%, about 97%, about 98%, about 98.5%, about 99.0%, about 99.5%, or about 99.9% weight per weight, weight per volume, or volume per volume of the final composition.

In some embodiments, the bacterial strain composition comprises a pharmaceutical composition wherein the bacterial strains provided herein are formulated as a pharmaceutical composition along with a pharmaceutically acceptable carrier. Such pharmaceutically acceptable carriers are known in the art and include an inert vehicle, adjuvants, preservatives etc., which are well known. In some embodiments, the pharmaceutically acceptable carrier comprises one that is not naturally-occurring (i.e., not found in nature). In particular embodiments, the pharmaceutically acceptable carrier is a naturally-occurring carrier that is not found with a bacterial strain of the invention in the native environment of the bacterial strain (i.e., a pharmaceutically acceptable carrier that is not naturally-occurring with a bacterial cell, spore, or forespore of a bacterial strain of the invention). Such pharmaceutical compositions can be prepared in accordance with known techniques. See, e.g., Remington, The Science and Practice of Pharmacy (21st ed. 2005).

In some embodiments, feed and/or food compositions can be prepared by combining a formulated bacterial strain of the invention with typical animal feed and/or food or drink ingredients. A formulated bacterial strain of the invention can be used for the preparation of animal feed or food products or beverages, and/or may be added to drinking and/or rearing water. In other embodiments, the compositions of the present invention are feed, food and/or drink additives that are added to a subject's feed, food, drinking water or beverage prior to ingestion.

As used herein, "animal feed" includes any animal feed blend known in the art, including rapeseed meal, cottonseed meal, soybean meal, cornmeal, barley, wheat, silage, and haylage.

The bacterial strains provided herein can be formulated as a food composition such as a dietary supplement, a functional food, a medical food or a nutritional product as long as the required effect is achieved, i.e. conversion of at least one glucosinolate to an isothiocyanate. Said food compositions may be chosen from the group consisting of beverages, yogurts, juices, ice creams, breads, biscuits, crackers, cereals, health bars, spreads, and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins.

In some embodiments, the bacterial strain composition disclosed herein is formulated as a liquid formulation or a solid formulation. When the bacterial strain composition (e.g., pharmaceutical composition) is a solid formulation, it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip, or a film. When the bacterial strain composition (e.g., pharmaceutical composition) is a liquid formulation, it may be formulated as an oral solution, a suspension, an emulsion or syrup. The composition may further comprise a carrier material independently selected from, but not limited to, the group consisting of vegetables, lactic acid fermented foods, fermented dairy products, resistant starch, dietary fibers, carbohydrates, proteins, and glycosylated proteins.

Additional beneficial microbes may be combined with a bacterial strain of the invention into a formulated product. Alternatively, additional formulated probiotics may be combined or mixed with a formulated bacterial strain of the invention into a feed or food composition, into drinking water, or into a pharmaceutical composition. Alternatively, the additional probiotic may be administered at a different time. These additional beneficial microbes may be selected from species of *Saccharomyces*, species of *Bacillus* such as *Bacillus subtilis, Bacillus licheniformis, Bacillus lentus, Bacillus pumilus, Bacillus laterosporus, Bacillus coagulans, Bacillus alevi, Bacillus cereus, Bacillus clausii, Bacillus coagulans, Bacillus inaquosorum, Bacillus mojavensis, Bacillus velezensis, Bacillus vallismortis, Bacillus amyloliquefaciens, Bacillus atropheus, Bacillus altitudinis, Bacillus safensis, Bacillus alcalophilus, Bacillus badius,* or *Bacillus thurigiensis*; from species of *Enterococcus* such as *Enterococcus faecium*; from species of *Clostridium* such as *Clostridium butyricum*; from species of *Lactococcus* such as *Lactococcus lactis* or *Lactoccus cremoris*; from species of *Bifidobacterium* such as *Bifidobacterium adolescentis, Bifidobacterium animalis, Bifidobacterium bifidum, Bifidobacterium infantis, Bifidobacterium longum, Bifidobacterium pseudolongum,* or *Bifidobacterium thermophilum*; from species of *Lactobacillus* such as *Lactobacillus alactosus, Lactobacillus alimentarius, Lactobacillus amylovorans, Lactobacillus amylophilus, Lactobacillus amylovorans, Lactobacillus acidophilus, Lactobacillus agilis, Lactobacillus animalis, Lactobacillus batatas,* Lactobacillusbavaricus, *Lactobacillus bifermentans, Lactobacillus bidifus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus curvatus, Lactobacillus coprohilus, Lactobacillus delbrueckii, Lactobacillus fermentum, Lactobacillus gasseri, Lactobacillus jugurti, Lactobacillus kefir, Lactobacillus lactis, Lactobacillus leichmannii, Lactobacillus mali, Lactobacillus malefermentans, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus tolerans, Lactoba-*

*cillus torquens, Lactobacillus ruminis, Lactobacillus sake, Lactobacillus saliverius, Lactobacillus sharpeae, Lactobacillus sobrius, Lactobacillus trichodes, Lactobacillus vaccinostercus, Lactobacillus viridescens, Lactobacillus vitulinus, Lactobacillus xylosus, Lactobacillus yamanashiensis,* or *Lactobacillus zeae*; from species of Megasphaera such as *Megasphaera elsdenil*; from species of Prevotella such as *Prevotella bryantii*; from species of Pediococcus such as *Pediococcus acidilactici*, or *Pediococcus pentosaceus*; from species of Streptococcus such as *Streptococcus cremoris, Streptococcus discetylactis, Streptococcus faecium, Streptococcus lactis, Streptococcus thermophilus,* or *Streptococcus intermedius*; or from species of Propionibacterium such as *Propionibacterium freudenreichii, Propionibacterium acidipropionici, Propionibacterium jensenii, Propionibacterium thoenii, Propionibacterium australiense,* or *Propionibacterium avidum,* and/or a combination thereof.

Compositions of the invention may also include prebiotics, which may be combined or mixed with a formulated bacterial strain of the invention into a feed or food composition, into drinking water, or into a pharmaceutical composition. Prebiotics are food ingredients that are not readily digestible by enzymes endogenous to the gut (such as those expressed by the animal or those expressed by the resident gut microbiome) and that selectively stimulate the growth and activity of selected groups of intestinal microorganisms that confer beneficial effects upon their host. Typically, it is beneficial microorganism populations that benefit from the presence of prebiotic compounds. Prebiotics can consist of oligosaccharides and other small molecules that serve as metabolic substrates for growth of beneficial microbes. Common prebiotics include galacto-oligosaccharides, fructo-oligosaccharides, inulin, isomalto-oligosaccharies, gentio-oligosaccharides, lactilol, lactosucrose, lactulose, xylosucrose, glycosyl sucrose, pyrodextrins, soybean oligosaccharides, guar gum, locust bean gum, arabinan, galactan, pectins, and pectic polysaccharides. While many diverse microbes inhabit the intestinal tract of a host organism, prebiotic compounds are only utilized by the beneficial microbes and lead to a selective enhancement of the beneficial microbe population. A formulation that includes both prebiotics and probiotics may be known as a "synbiotic".

In certain embodiments, the bacterial strain composition comprises at least one glucosinolate. Non-limiting examples of glucosinolates include those that are described elsewhere herein. In some embodiments, the bacterial strain composition comprises glucosinolate at an amount of about 1 μg to about 1 g, including but not limited to about 1 μg to about 2 μg, about 300 μg to about 100 mg, about 350 μg to about 30 mg, about 1 μg, about 2 μg, about 5 μg, about 10 μg, about 20 μg, about 25 μg, about 50 μg, about 100 μg, about 200 μg, about 300 μg, about 400 μg, about 500 μg, about 600 μg, about 700 μg, about 800 μg, about 900 μg, about 1 mg, about 2 mg, about 5 mg, about 10 mg, about 20 mg, about 25 mg, about 50 mg, about 100 mg, about 200 mg, about 300 mg, about 400 mg, about 500 mg, about 600 mg, about 700 mg, about 800 mg, about 900 mg, and about 1 g. In certain embodiments, the bacterial strain composition comprises a plant, plant part or extract thereof that comprises the glucosinolate(s). The glucosinolate may be synthetically produced or derived from a natural source. Glucosinolates are found in a variety of plants, both cruciferous and non-cruciferous. Generally, angiosperm families that contain glucosinolate chemicals include: Bataceae, Brassicaceae, Bretschneideraceae, Capparaceae, Caricaceae, Euphorbiaceae, Gyrostemonaceae, Limnanthaceae, Moringaceae, Pentadiplandraceae, Phytolaccaceae, Pittosporaceae, Resedaceae, Salvadoraceae, Tovariaceae, and Tropaeolaceae. Glucosinolates are found in abundance in the seeds and sprouts of many species of the above-mentioned families. Most of the plants containing glucosinolate fall within the Brassicaceae, Capparaceae, and Caricaeae families (Fahey et al. Phytochemistry (2001) 56:5-51, which is herein incorporated by reference in its entirety).

In some embodiments, the bacterial strain composition comprises a cruciferous plant, plant part, or extract thereof. As used herein, the term "cruciferous plant" or "cruciferous plant part" refers to plants or plant parts within the Brassicaceae family (also referred to as the Cruciferae family). In some embodiments, the cruciferous plant belongs to the genus Brassica. In some of these embodiments, the cruciferous plant is a *Brassica oleracea*, including but not limited to varieties *acephala* (kale, collards, wild cabbage, curly kale), *capitate* (cabbage), *medullosa* (marrowstem kale), *ramosa* (thousand head kale), *alboglabra* (Chinese kale), *botrytis* (cauliflower, sprouting broccoli, broccoli romanesco), *costata* (Portuguese kale), *gemmifera* (Brussels sprouts), *gongylodes* (kohlrabi), *italica* (broccoli, broccolini, broccoflower), *palmifolia* (Jersey kale), *sabauda* (savoy cabbage), *sabellica* (collards), and *selensia* (borecole), among others. In other embodiments, the cruciferous plant is a *Brassica rapa*, including but not limited to *Brassica rapa chinensis* (bok choy), *Brassica rapa perviridis* (komatsuna), *Brassica rapa nipposinica* (mizuna), *Brassica rapa parachinensis* (rapini, choy sum), *Brassica rapa pekinensis* (Chinese cabbage), and *Brassica rapa rapifera* (turnip root and greens). In still other embodiments, the cruciferous plant is a *Brassica napus* (including but not limited to *Brassica napus napobrassica* (rutabaga), *Brassica napus pabularia* (Siberian kale), *Brassica napus oleifera* (canola/rapeseed), *Brassica juncea* (including but not limited to brown mustard seeds and greens and *Brassica juncea rugosa*), *Brassica hirta* (white mustard seeds), *Brassica nigra* (black mustard seeds), *Brassica rosularis* (tatsoi), and *Brassica carinata* (Ethiopian mustard). In yet other embodiments, the cruciferous plant is *Armoracia rusticana* (horseradish), *Barbarea verna* (land cress), *Diplotaxis tenuifolia* (wild arugula), *Eruca vesicaria* (arugula), *Lepidium campestre* (field pepperweed), *Lepidium meyenii* (maca), *Lepidium sativum* (garden cress), *Nasturtium officinale* (watercress), *Raphanus sativus* (radish), *Raphanus sativus longipinnatus* (daikon), and *Wasabia japonica* (wasabi).

Plant sources suitable for use in the methods and compositions disclosed herein may be any part of a plant, including, but not limited to cells, seeds, sprouts, leaves, stalks, roots, flowers, and other plant structures.

Glucosinolates can also be obtained from extracts of any of the above-mentioned species of plants or parts therefrom. As used herein, an "extract" of a plant or plant part refers to concentrated preparations comprising a desired active compound derived from the plant or plant part using any method known in the art, including but not limited to solvent extraction, distillation method, pressing and sublimation (see, e.g., Zhang et al. (2018) *Chin Med.* 13:20). According to the presently disclosed methods and compositions, the extract of a plant or plant part can comprise an active myrosinase enzyme able to convert a glucosinolate to an isothiocyanate.

Bacterial compositions of the invention can comprise an enzyme potentiator (i.e., cofactor). Enzyme potentiators may be used to enhance the activity of myrosinase. In some embodiments, the enzyme potentiator comprises ascorbic acid, also known as ascorbate or vitamin C, which serves as a base catalyst in glucosinolate hydrolysis. In some embodiments, without an enzyme potentiator such as ascorbic acid, the conversion reaction to sulforaphane may be too slow to occur in the location needed for peak absorption. The enzyme potentiator may be obtained from a natural source, or it may be produced synthetically.

In some embodiments, the bacterial strain composition comprises a concentration of the bacterial strain of at least about $10^4$ CFU/g to about $10^{12}$ CFU/g, about $10^5$ CFU/g to about $10^{12}$ CFU/g, about $10^6$ CFU/g to about $10^{12}$ CFU/g, about $10^7$ CFU/g to about $10^{12}$ CFU/g, about $10^8$ CFU/g to about $10^{12}$ CFU/g, about $10^9$ CFU/g to about $10^{12}$ CFU/g, about $10^{10}$ CFU/g to about $10^{12}$ CFU/g, about $10^{11}$ CFU/g to about $10^{12}$ CFU/g, about $10^5$ CFU/g to about $10^{11}$ CFU/g, about $10^5$ CFU/g to about $10^{11}$ CFU/g, about $10^6$ CFU/g to about $10^{11}$ CFU/g, about $10^7$ CFU/g to about $10^{11}$ CFU/g, about $10^8$ CFU/g to about $10^{11}$ CFU/g, about $10^9$ CFU/g to about $10^{11}$ CFU/g, about $10^{10}$ CFU/g to about $10^{11}$ CFU/g, about $10^5$ CFU/g to about $10^{10}$ CFU/g, about $10^6$ CFU/g to about $10^{10}$ CFU/g, about $10^7$ CFU/g to about $10^{10}$ CFU/g, about $10^8$ CFU/g to about $10^{10}$ CFU/g, or about $10^9$ CFU/g to about $10^{10}$ CFU/g. In other embodiments, the concentration of the bacterial strain provided herein or active variant thereof comprises or consists of at least about $10^4$ CFU/g, at least about $10^5$ CFU/g, at least about $10^6$ CFU/g, at least about $10^7$ CFU/g, at least about $10^8$ CFU/g, at least about $10^9$ CFU/g, at least about $10^{10}$ CFU/g, at least about $10^{11}$ CFU/g, or at least about $10^{12}$ CFU/g.

In liquid compositions and formulations, the amount of bacterial strain, or active variant thereof, disclosed herein can comprise a concentration of at least about $10^4$ CFU/ml to about $10^{12}$ CFU/ml, about $10^5$ CFU/ml to about $10^{12}$ CFU/ml, about $10^6$ CFU/ml to about $10^{12}$ CFU/ml, about $10^7$ CFU/ml to about $10^{12}$ CFU/ml, about $10^8$ CFU/ml to about $10^{12}$ CFU/ml, about $10^9$ CFU/ml to about $10^{12}$ CFU/ml, about $10^{10}$ CFU/ml to about $10^{12}$ CFU/ml, about $10^{11}$ CFU/ml to about $10^{12}$ CFU/ml, about $10^5$ CFU/ml to about $10^{11}$ CFU/ml, about $10^5$ CFU/ml to about $10^{11}$ CFU/ml, about $10^6$ CFU/ml to about $10^{11}$ CFU/ml, about $10^7$ CFU/ml to about $10^{11}$ CFU/ml, about $10^8$ CFU/ml to about $10^{11}$ CFU/ml, about $10^9$ CFU/ml to about $10^{11}$ CFU/ml, about $10^{10}$ CFU/ml to about $10^{11}$ CFU/ml, about $10^5$ CFU/ml to about $10^{10}$ CFU/ml, about $10^6$ CFU/ml to about $10^{10}$ CFU/ml, about $10^7$ CFU/ml to about $10^{10}$ CFU/ml, about $10^8$ CFU/ml to about $10^{10}$ CFU/ml, or about $10^9$ CFU/ml to about $10^{10}$ CFU/ml. In other embodiments, the concentration of the bacterial strain provided herein or active variant thereof comprises or consists of at least about $10^4$ CFU/ml, at least about $10^5$ CFU/ml, at least about $10^6$ CFU/ml, at least about $10^7$ CFU/ml, at least about $10^8$ CFU/ml, at least about $10^9$ CFU/ml, at least about $10^{10}$ CFU/ml, at least about $10^{11}$ CFU/ml, or at least about $10^{12}$ CFU/ml.

III. Methods of Administration of Bacterial Strains

Methods are provided herein for increasing the production of isothiocyanate from at least one glucosinate with an effective amount of a bacterial strain composition comprising a bacterial strain of the invention. The methods comprise contacting at least one glucosinolate with an effective amount of a bacterial strain composition comprising a bacterial strain of the invention. These methods can be performed in vitro, in vivo, or ex vivo. When performed in vivo, the method comprises administering to a subject an effective amount of a bacterial strain composition of the invention or an active variant thereof.

In specific embodiments, a bacterial strain composition is combined with at least one glucosinolate to increase the production of isothiocyanate when compared to an appropriate control (e.g., a sample prior to the addition of a bacterial strain composition). As used herein an "effective amount" refers to a quantity of a bacterial strain composition comprising a bacterial strain of the invention that increases the production of isothiocyanate from at least one glucosinolate when compared to an appropriate control (e.g., a sample prior to the addition of a bacterial strain composition). In some embodiments, an effective amount of the bacterial strain composition increases the expression of genes regulated by the Nrf2 transcription factor when compared to an appropriate control, such as phase II enzymes, decreases inflammation in a subject when compared to an appropriate control, or treats an inflammatory disorder or a cancer.

An effective amount of the bacterial strain composition (e.g., pharmaceutical composition) is determined based on the intended goal. The term "unit dose" refers to a physically discrete unit suitable for use in a subject or agricultural animal, each unit containing a predetermined quantity of the bacterial strain composition calculated to produce the desired response in association with its administration, i.e., the appropriate route and treatment regimen. The quantity to be administered, both according to number of treatments and unit dose, depends on the subject to be treated, the state of the subject, the environmental conditions of the subject, and the result desired. Precise amounts of the bacterial strain composition also depend on the judgment of the practitioner and can be unique to each individual.

In specific embodiments, the effective amount of a bacterial strain, or active variant thereof, disclosed herein is at least about $10^4$ CFU to about $10^{12}$ CFU, about $10^5$ CFU to about $10^{12}$ CFU, about $10^6$ CFU to about $10^{12}$ CFU, about $10^7$ CFU to about $10^{12}$ CFU, about $10^8$ CFU to about $10^{12}$ CFU, about $10^9$ CFU to about $10^{12}$ CFU, about $10^{10}$ CFU to about $10^{12}$ CFU, about $10^{11}$ CFU to about $10^{12}$ CFU, about $10^5$ CFU to about $10^{11}$ CFU, about $10^5$ CFU to about $10^{11}$ CFU, about $10^6$ CFU to about $10^{11}$ CFU, about $10^7$ CFU to about $10^{11}$ CFU, about $10^8$ CFU to about $10^{11}$ CFU, about $10^9$ CFU to about $10^{11}$ CFU, about $10^{10}$ CFU to about $10^{11}$ CFU, about $10^5$ CFU to about $10^{10}$ CFU, about $10^6$ CFU to about $10^{10}$ CFU, about $10^7$ CFU to about $10^{10}$ CFU, about $10^8$ CFU to about $10^{10}$ CFU, or about $10^9$ CFU to about $10^{10}$ CFU. In other embodiments, the effective amount is at least about $10^4$ CFU, at least about $10^5$ CFU, at least about $10^6$ CFU, at least about $10^7$ CFU, at least about $10^8$ CFU, at least about $10^9$ CFU, at least about $10^{10}$ CFU, at least about $10^{11}$ CFU, or at least about $10^{12}$ CFU.

In certain embodiments, a bacterial strain or an active variant thereof disclosed herein is administered to a subject that is also administered (simultaneously or sequentially) an additional beneficial microbe. Additional beneficial microbes, such as those described elsewhere herein, may be combined with a bacterial strain of the invention into a formulated product or the beneficial microbes may be administered separately from (before, during, or after) a bacterial strain of the invention.

In some embodiments, a bacterial strain or an active variant thereof disclosed herein is administered to a subject that is also administered (simultaneously or sequentially) a prebiotic. Prebiotics, such as those described elsewhere herein, may be combined with a bacterial strain of the invention into a formulated product or the prebiotic(s) may be administered separately from (before, during, or after) a bacterial strain of the invention.

In particular embodiments, a bacterial strain or an active variant thereof disclosed herein is administered to a subject that is also administered (simultaneously or sequentially) a glucosinolate or a plant, plant part or extract thereof comprising a glucosinolate. Glucosinolates, plants, plant parts, or extracts thereof, such as those described elsewhere herein, may be combined with a bacterial strain of the invention into a formulated product or the glucosinolate, plant, plant part, or extract thereof, may be administered separately from (before, during, or after) a bacterial strain of the invention. In some of these embodiments, glucosinolates are administered in an amount ranging about 1 µg to about 1 g, including but not limited to about 1 µg to about 2 µg, about 300 to about 100 mg, about 350 µg to about 30 mg, about 1 µg, about 2 µg, about 5 µg, about 10 µg, about 20 µg, about 25 µg, about 50 µg, about 100 µg, about 200 µg, about 300 µg, about 400 µg, about 500 µg, about 600 µg, about 700 µg, about 800 µg, about 900 µg, about 1 mg, about 2 mg, about 5 mg, about 10 mg, about 20 mg, about 25 mg, about 50 mg, about 100 mg, about 200 mg, about 300 mg, about 400 mg, about 500 mg, about 600 mg, about 700 mg, about 800 mg, about 900 mg, and about 1 g.

In those embodiments wherein the beneficial microbe, prebiotic, glucosinolate, plant, plant part, or extract thereof is administered separately from a bacterial strain of the invention, the bacterial strain composition may be administered before, during, or after the beneficial microbe, prebiotic, glucosinolate, plant, plant part, or extract thereof. The bacterial strain of the invention and the additional component (e.g., beneficial microbe, prebiotic, glucosinolate, plant, plant part, or extract thereof) can be administered to a subject within minutes (e.g., 1, 2, 5, 10, 15, 30, 45 minutes), hours (e.g., 1, 2, 3, 4, 5, 6, 7, 8, 9, 10, 12, 15, 20 hours), or days (e.g., 1, 2, 3, 4, 5, 6, 7 days) of each other.

As used herein, the bacterial strain composition can be used to increase the production of isothiocyanate from at least one glucosinolate in any subject when compared to an appropriate control (e.g., a sample from the subject prior to administration of a bacterial strain composition). By "subject" is intended animals. In specific embodiments, subjects are mammals, e.g., primates or humans. In other embodiments, subjects include domestic animals, such as a feline or canine, or agricultural animals, such as a ruminant, horse, swine, poultry, or sheep.

As used herein, an "increase in" or "increasing" isothiocyanate production comprises any statistically significant increase in the level of isothiocyanate when compared to an appropriate control (e.g., a corresponding sample not contacted with a bacterial strain composition). Such increases can include, for example, at least a 5%, 10%, 20%, 30%, 40%, 50%, 60%, 70%, 80%, 90%, 100%, 150%, 200% or greater increase in the isothiocyanate level when compared to an appropriate control. Such increases can also include, for example, at least about a 3%-15%, 10%-25%, 20% to 35%, 30% to 45%, 40%-55%, 50%-65%, 60%-75%, 70%-85%, 80%-95%, 90%-105%, 100%-115%, 105%-120%, 115%-130%, 125%-150%, 140%-160%, 155%-500% or greater increase in the isothiocyanate level when compared to an appropriate control. Isothiocyanate levels can be measured in a bacterial composition. In some embodiments, the level of isothiocyanate can be measured in a sample taken from a subject, or measured directly in the subject. In specific embodiments, the level of isothiocyanate is measured in an intestine, colon, blood, urine, or fecal sample taken from a subject.

In specific embodiments, an increase in isothiocyanate production is measured in reference to the level of isothiocyanate in a proper control sample. As used herein, a proper control includes but is not limited to, the level of isothiocyanate in a corresponding sample that does not comprise a bacterial strain of the invention, the level of isothiocyanate from a subject that was not administered a bacterial strain composition comprising a bacterial strain of the invention, the level of isothiocyanate in a sample from the subject prior to administration of a bacterial strain composition comprising a bacterial strain of the invention, or the level of isothiocyanate in a standardized sample from a subject that was not administered a bacterial strain composition comprising a bacterial strain of the invention. One of skill in the art would be able to identify proper controls in order to measure an increase in the level of isothiocyanate.

Thus, the presently disclosed methods comprise increasing isothiocyanate production by contacting at least one glucosinolate with an effective amount of a bacterial strain composition comprising a bacterial strain of the invention when compared to an appropriate control, which can be the level of isothiocyanate in a corresponding sample that does not comprise a bacterial strain of the invention, the level of isothiocyanate from a subject that was not administered a bacterial strain composition comprising a bacterial strain of the invention, the level of isothiocyanate in a sample from the subject prior to administration of a bacterial strain composition comprising a bacterial strain of the invention, or the level of isothiocyanate in a standardized sample from a subject that was not administered a bacterial strain composition comprising a bacterial strain of the invention.

When glucosinolates are hydrolyzed to isothiocyanates, isothiocyanates are then rapidly metabolized via conjugation with glutathione and these conjugates then undergo stepwise hydrolysis, leading ultimately to N-acetylcysteine derivatives (i.e., mercapturic acids). These conjugates are known as dithiocarbamates, which can be quantified by the cyclocondensation reaction (Ye et al. (2002) *Clinica Chimica Acta* 316(1-2):43-53, which is incorporated by reference in its entirety). The cyclocondensation reaction involves reacting isothiocyanates and dithiocarbamates with 1,2-benzenedithiol to produce 1,3-benzodithiole-2-thione that can then be quantified spectroscopically using high performance liquid chromatography (HPLC), or mass spectrometry.

An isothiocyanate (e.g., sulforaphane) can be positively identified by comparison of the retention time and UV spectrum to authentic chemical standards. See, for example, Ye et al. (2002), which is herein incorporated by reference in its entirety.

The bacterial strain composition can be administered to a subject based on standard techniques known in the art for administration to the particular type of subject and in the environment in which the subject receives the bacterial strain composition. When administered to a human, the bacterial strain composition may be a liquid formulation or a solid formulation. The bacterial strain composition can be administered mucosally via oral administration, nasal administration, or rectal administration, for example, or administered parenterally, including but not limited to subcutaneous administration, transdermal administration, or any method that allows a bacterial strain of the invention to come into contact with at least one glucosinolate.

In some embodiments of the invention, the method comprises administration of multiple doses of the bacterial composition to a subject. The method may comprise administration of 1, 2, 3, 4, 5, 6, 7, 8, 9, 10, 15, 20, 25, 30, 35, 40, or more effective doses of a bacterial strain composition comprising *B. subtilis* 1579 as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as to increase the production of isothiocyanate when compared to an appropriate control. It will also be appreciated that the effective amount or dosage of a bacterial strain composition may increase or decrease over the course of a particular treatment. Changes in dosage may result and become apparent from the results of diagnostic assays for detecting isothiocyanate level known in the art and described herein.

As used herein, "treatment" or "treating" refers to therapeutic (e.g., curing, healing, alleviating, relieving, altering, remedying, ameliorating, improving, or affecting the condition or the symptoms of a subject) and preventative effects. The prophylactic administration (wherein a bacterial strain of the invention is administered in advance of symptoms) serves to prevent or attenuate any subsequent symptom. When provided therapeutically, the bacterial strain composition is provided at (or shortly after) the onset of a symptom. The therapeutic administration of the substance may serve to attenuate any actual symptom.

A. Methods of Increasing Expression of Nrf2-Regulated Genes

Methods are provided herein for increasing the expression of genes that are regulated by the Nrf2 transcription factor by contacting a cell with an effective amount of a bacterial composition comprising a bacterial strain of the invention and at least one glucosinolate. There are estimated to be about 500 genes that are upregulated by Nuclear factor E2-related factor 2 (Nrf2), many of which comprise an antioxidant response element (ARE) in their regulatory regions (Wasserman and Fahl (1997) *PNAS* 94(10):5361-5366, which is herein incorporated by reference in its entirety). The longest isoform (isoform 1) of human Nrf2 protein is set forth as GenBank Acc. No. NP_006155. Genes regulated by Nrf2 include but are not limited to glucose 6-phosphate dehydrogenase, 6-phosphogluconate dehydrogenase, malic enzyme, glutathione peroxidase, glutathione reductase, ferritin, and haptaglobin (see, e.g., Thimmulappa et al. (2002) *Cancer Research* 62(18):5196-5203, which is herein incorporated by reference in its entirety). Nrf2 regulates the expression and activation of phase II enzymes, which are enzymes responsible for the biotransformation and conjugation of drugs, xenobiotics, and some endogenous substrates with charged species such as glutathione, sulfate, glycine, or glucuronic acid. Phase II enzymes include but are not limited to UDP-glucuronosyltransferases, sulfotransferases, N-acetyltransferases, epoxide hydrolase, glutathione-S-transferases, methyltransferases, NAD(P)H:quinone oxidoreductase-1, heme oxygenase-1 and γ-glutamylcysteine synthase (see, e.g., Chen and Kunsch (2004) *Current Pharmaceutical Design* 10(8):879-891, which is herein incorporated by reference in its entirety).

Any cell comprising the Nrf2 transcription factor may be contacted with a bacterial composition of the invention to increase the expression of genes regulated by Nrf2 when compared to an appropriate control (e.g., a cell prior to contact with a bacterial strain composition), but in some embodiments, the cell is an intestinal cell, liver cell, kidney cell, lung cell, skin cell, or adipose cell.

As used herein, an "increase in" or "increasing" expression of a gene comprises any statistically significant increase in the gene product, including the mRNA or protein, when compared to an appropriate control (e.g., a cell prior to contact with a bacterial strain composition). Such increases can include, for example, at least a 5%, 10%, 20%, 30%, 40%, 50%, 60%, 70%, 80%, 90%, 100%, 150%, 200% or greater increase in the level of the gene product when compared to an appropriate control. Such increases can also include, for example, at least about a 3%-15%, 10%-25%, 20% to 35%, 30% to 45%, 40%-55%, 50%-65%, 60%-75%, 70%-85%, 80%-95%, 90%-105%, 100%-115%, 105%-120%, 115%-130%, 125%-150%, 140%-160%, 155%-500% or greater increase in the level of the gene product when compared to an appropriate control. The expression of a gene regulated by Nrf2, such as those comprising an ARE in their regulatory regions, can be measured by measuring the levels of the gene product, such as measuring mRNA levels or protein levels. Any method known in the art can be used to measure mRNA levels, including but not limited to, quantitative polymerase chain reaction (qPCR), reverse transcription following by qPCR (RT-qPCR), and Northern blot, and any method known in the art can be used to measure protein levels, including but not limited to, Western blot and ELISA.

As used herein a proper control includes but is not limited to, the expression level of a gene in a corresponding cell or sample of cells (e.g., biological sample from a subject) that was not contacted with the bacterial strain composition comprising a bacterial strain of the invention and at least one glucosinolate, the expression level of a gene in a cell or a sample of cells that was not contacted with the bacterial strain composition comprising a bacterial strain of the invention and at least one glucosinolate, or the expression level of a gene in a standardized cell or sample of cells that was not contacted with the bacterial strain composition comprising a bacterial strain of the invention and at least one glucosinolate. One of skill in the art would be able to identify proper controls in order to measure an increase in the expression level of a gene in a cell or sample of cells.

B. Methods of Decreasing Inflammation

Compositions and methods are provided herein for decreasing inflammation in a subject by administering a bacterial strain composition comprising a bacterial strain of the invention, and in some embodiments at least one glucosinolate or a plant, plant part, or extract thereof comprising a glucosinolate. In some embodiments, administration of a bacterial strain composition comprising a bacterial strain of the invention can treat an inflammatory disease, and particularly can ameliorate the symptoms or prevent an inflammatory disease of the gastrointestinal tract, such as an inflammatory bowel disease (IBD), including, but not limited to, Crohn's disease and/or colitis (e.g., ulcerative colitic), in a subject. In some embodiments, administration of a bacterial strain composition comprising a bacterial strain of the invention can treat an inflammatory disease, and particularly can ameliorate the symptoms or prevent a systemic inflammatory disorder outside the gastrointestinal tract, such as rheumatoid arthritis, systemic lupus erythematosus and/or multiple sclerosis, in a subject. The systemic inflammatory disorder can be any inflammatory disorder and need not be associated with gastrointestinal inflammation. The subject to be treated can be suffering from or at risk of developing a gastrointestinal disorder, including, for example, be suffering from an inflammatory bowel disease or be at risk of developing an inflammatory bowel disease.

In some embodiments, the reduction or decrease in inflammation may include stimulation of intestinal integrity; reduction of intestinal permeability; improvement of mucin synthesis, secretion, and/or quality; improvement of the maturation and differentiation of the intestinal epithelium; improvement of nutrient absorption; increase of the production of soluble factors that transfer antimicrobial activity; stimulation of, improvement of, or support of resistance to infection; support of cellular or humoral responses against viral or bacterial infection; increased cytotoxicity (both anti-viral and anti-tumor); support of systemic and/or mucosal vaccination responses; increase or support of cellular and/or humoral immunity; increase or support of natural immunity (including neutrophils, phagocytes, macrophages, and natural killer cell activity); increase or support of adaptive T and B cell immunity; stimulation of a helper T cell 1 (Th1) cytokine pattern (increased IL-1, IL-2, IFN-gamma, IL-12, TNF-alpha; human leukocyte antigen-Dr (HLA-Dr) expression); suppression of inflammation or production of systemic and mucosal inflammatory mediators (including cytokines and/or chemokines); reduction of sensitization by reducing total and/or allergen-specific IgE; reduction of the production of allergic cytokines; reduction of a Th2 supporting immunoglobulin profile; and combinations thereof when compared to an appropriate control (e.g., a sample from a subject prior to administration of a bacterial strain composition).

As used herein, the term "anti-inflammatory cytokine" refers to a naturally occurring or recombinant protein, analog thereof or fragment thereof that elicits an anti-inflammatory response in a cell that has a receptor for that cytokine. Anti-inflammatory cytokines of the invention can be immunoregulatory molecules that control the proinflammatory cytokine response. Anti-inflammatory cytokines of the invention include interleukin (IL)-1 receptor antagonist, IL-4, IL-10, IL-11, and IL-13, IL-16, IFN-alpha, TGF-beta, G-CSF.

As used herein, the term "proinflammatory cytokine" refers to an immunoregulatory cytokine that favors inflammation. Proinflammatory cytokines of the invention include IL1-alpha, IL1-beta, TNF-alpha, IL-2, IL-3, IL-6, IL-7, IL-9, IL-12, IL-17, IL-18, LT, LIF, Oncostatin, or IFN-alpha, IFN-beta, IFN-gamma.

In some embodiments, administration of the bacterial strain composition results in an increase in anti-inflammatory cytokine production. As used herein, an "increase in" or "increasing" anti-inflammatory cytokine production comprises any statistically significant increase in the anti-inflammatory cytokine level when compared to an appropriate control. Such increases can include, for example, at least a 5%, 10%, 20%, 30%, 40%, 50%, 60%, 70%, 80%, 90%, 100%, 150%, 200% or greater increase in the anti-inflammatory cytokine level when compared to an appropriate control. Such increases can also include, for example, at least about a 3%-15%, 10%-25%, 20% to 35%, 30% to 45%, 40%-55%, 50%-65%, 60%-75%, 70%-85%, 80%-95%, 90%-105%, 100%-115%, 105%-120%, 115%-130%, 125%-150%, 140%-160%, 155%-500% or greater increase in the anti-inflammatory cytokine level when compared to an appropriate control. Methods to assay for the level of anti-inflammatory cytokine level, are known. See, for example, Leng S., et al. (2008) *J Gerontol A Biol Sci Med Sci* 63(8): 879-884. Methods to assay for the production of anti-inflammatory cytokines include multiplex bead assay, ELISA, ELISPOT, qPCR, and flow cytometry. See, for example, Maecker et al. (2005) *BMC Immunology* 6:13.

Methods and compositions also include those which decrease proinflammatory cytokine production, which may decrease or prevent an inflammatory response. As used herein, a decrease in the level of pro-inflammatory cytokine production comprises any statistically significant decrease in the level of pro-inflammatory cytokine production in a subject when compared to an appropriate control. Such decreases can include, for example, at least a 5%, 10%, 20%, 30%, 40%, 50%, 60%, 70%, 80%, 90%, or 100% decrease in the level of proinflammatory cytokines when compared to an appropriate control. Methods to assay for cytokine levels are known and include, for example Leng S., et al. (2008) *J Gerontol A Biol Sci Med Sci* 63(8): 879-884. Methods to assay for the production of pro-inflammatory cytokines include multiplex bead assay, ELISPOT and flow cytometry. See, for example, Maecker et al. (2005) *BMC Immunology* 6:13.

Inflammatory cytokine production can also be measured by assaying the ratio of anti-inflammatory cytokine production to proinflammatory cytokine production. In specific aspects, the ratio of anti-inflammatory cytokine production to proinflammatory cytokine production is increased by about 1, 2, 3, 4, 5, 6, 7, 8, 9, 10, 20, 30, 40, 50, 60, 70, 80, 90, 100, 300, 600, 900, 1000 fold or greater when compared to an appropriate control. In other aspects, the ratio of anti-inflammatory cytokine production to pro-inflammatory cytokine production is increased by about 1 to 5 fold, about 5 to 10 fold, about 10 to 20 fold, about 20 to 30 fold, about 30 to 40 fold, about 40 fold to 60 fold, about 60 fold to 80 fold, about 80 fold to about 100 fold, about 100 to 200 fold, about 200 fold to 300 fold, about 300 to 400 fold, about 400 to about 500 fold, about 500 to about 500 fold, about 500 fold to about 700 fold, about 700 fold to 800 fold, about 800 fold to about 1000 fold or greater when compared to an appropriate control. Methods to determine the ratio of anti-inflammatory cytokine production to pro-inflammatory cytokine production can be found, for example, Leng S., et al. (2008) *J Gerontol A Biol Sci Med Sci* 63(8): 879-884. Methods to assay for the production of cytokines include multiplex bead assay, ELISA, ELISPOT, qPCR, and flow cytometry. See, for example, Maecker et al. (2005) *BMC Immunology* 6:13.

In specific embodiments, administration of an effective amount of the bacterial strain composition comprising a bacterial strain of the invention can decrease the expression of a marker of inflammation compared to a proper control. Such decreases can include, for example, at least a 5%, 10%, 20%, 30%, 40%, 50%, 60%, 70%, 80%, 90%, or 100% decrease in the level of expression of a marker of inflammation, as measured by mRNA level, qPCR, protein level, ELISA, LPS expression, or any method known in the art, when compared to an appropriate control. The level of the inflammation marker can be measured as it relates to a proper control. As used herein a proper control includes but is not limited to, the expression level of a marker of inflammation in a corresponding sample from a subject that was not administered the bacterial strain composition comprising a bacterial strain of the invention, the expression level of a marker of inflammation in a sample from a subject prior to administration of the bacterial strain composition comprising a bacterial strain of the invention, or the expression level of a marker of inflammation in a standardized sample from a subject that was not administered the bacterial strain composition comprising a bacterial strain of the invention. One of skill in the art would be able to identify proper controls in order to measure an increase in the expression level of a marker of inflammation in a human subject or agricultural animal.

C. Methods for Treating Cancer

Methods are provided herein for treating cancer in a subject by administering a bacterial strain composition comprising a bacterial strain of the invention, and in some embodiments at least one glucosinolate or a plant, plant part, or extract thereof comprising a glucosinolate.

While not wishing to be bound to any theory or mechanism of action, it is believed that the chemopreventive effects of isothiocyanates are related to the ability to activate phase II detoxification enzymes and isothiocyanates also have inhibitory effects on the growth of various types of cancer cells and can induce apoptosis of cancer cells possibly through inhibition of histone deacetylation. See, for example, Wu et al. (2009) *Acta Pharmacol Sin.* 30(5):501-512.

As used herein, the term "cancer" should be understood to encompass any neoplastic disease (whether invasive or metastatic) which is characterized by abnormal and uncontrolled cell division causing malignant growth or tumor. Cancers that may be treated with the presently disclosed compositions and methods include tumors that are not vascularized, or not yet substantially vascularized, as well as vascularized tumors. The cancers may include non-solid tumors (such as hematological tumors, for example, leukemias and lymphomas) or may include solid tumors. Non-limiting examples of types of cancers to be treated with the presently disclosed compositions and methods include, but are not limited to, carcinoma, blastoma, and sarcoma, and certain leukemia or lymphoid malignancies, benign and malignant tumors, and malignancies such as sarcomas, carcinomas, and melanomas. Other non-limiting examples include breast cancer, prostate cancer, ovarian cancer, cervical cancer, skin cancer, pancreatic cancer, colorectal cancer, renal cancer, liver cancer, brain cancer, lymphoma, leukemia, and lung cancer.

The subject to be treated can be suffering from or at risk of developing a cancer, including, for example, a subject with a genetic predisposition for cancer or a subject exposed to carcinogens. Subjects can be treated that have cancer of any clinical stage.

A cancer can be considered treated if the subject undergoes a complete or partial response, which can be determined by objective criteria commonly used in clinical trials for cancer, e.g., as listed or accepted by the National Cancer Institute and/or Food and Drug Administration. Non-limiting examples of such criteria include a reduction in the incidence and/or severity of symptoms, metastasis, or number of cancer cells. Such decreases can include, for example, at least a 5%, 10%, 20%, 30%, 40%, 50%, 60%, 70%, 80%, 90%, or 100% decrease in the incidence and/or severity of symptoms, metastasis, or number of cancer cells as compared to an appropriate control (e.g., a sample from a subject prior to administration of a bacterial strain composition).

As used herein a proper control includes but is not limited to, a corresponding sample from a subject that was not administered the bacterial strain composition comprising a bacterial strain of the invention, a subject prior to administration of the bacterial strain composition comprising a bacterial strain of the invention, or a standardized control.

The presently disclosed bacterial compositions can be administered along with (simultaneously or sequentially) any cancer treatment known in the art, including but not limited to radiation therapy and chemotherapeutic drugs.

The following examples are offered by way of illustration and not by way of limitation.

EXPERIMENTAL

Example 1: Isolation and Selection of Bacterial Strains with Myrosinase

Aerobic spore-forming bacteria and facultative anaerobic lactobacilli were isolated from a variety of environmental sources and stored at −80° C. Genomic DNA was isolated from each strain for genetic screening by detection of functional genes via PCR.

Materials and Methods

Isolation of bacteria: Samples from various environmental sources were diluted with 99 mL of sterile 0.1% peptone broth. To isolate spore-forming bacteria, some samples were subjected to spore-treatment in a 65° C. water bath for 30 min. Lactic acid bacteria were diluted as above. Serial dilutions of all samples were made and pour-plated with tempered molten TSA or MRS (Becton, Dickenson & Company, Franklin Lakes, N.J.) and incubated at 32° C. for 12-24 h or 37° C. for 48 hours. Several isolated colonies from each sample were picked and struck to the appropriate agar plates for isolation and incubated at 32° C. for 12-24 h or 37° C. for 48 hours. Isolated colonies were picked and used to inoculate 500 µl of respective culture media (Becton, Dickenson & Company, Franklin Lakes, N.J.) in a well of a 96-well culture block (Falcon, Tewksbury, Mass.) and incubated at 32° C. for 12-24 h or 37° C. for 48 h. Following incubation, 250 µl of the growth culture was spun down and resuspended in 2000 appropriate media with 20% glycerol. This mixture was frozen at −80° C. as frozen cell stock. The remaining 300 µl of growth culture was spun down and frozen at −20° C. to be used for gDNA isolation.

DNA Isolation: Genomic DNA was extracted from isolated strains using either the Roche *Applied Science* High Pure PCR Template Kit or the following DNA isolation protocol. 20 µL of lysozyme (100 mg/mL) was added to 300 µL of overnight growth in TSB or MRS and incubated at 37° C. for 60 min. 220 µL of lysis buffer (6 M Guanidine, 20% Triton-X 100, 10 mM Tris-HCl, pH 7.5) was added and incubated at 25° C. for 15 min. 20 µl of Protease K 800 U/ml (NEB, Ipswich, Mass.) was added and incubated at 55° for 30 min. 400 µL of lysate was transferred to a Wizard® SV 96 Binding Plate (Promega, Fitchburg, Wis.) and manufacturer's filtration instructions from the Wizard® SV 96 Genomic DNA Purification System were continued starting from step 3.C.4 (April 2015/revision) (Promega, Fitchburg, Wis.).

PCR Amplification: A library of over 3000 environmental bacteria was screened using genetic primers. Two primer/probe sets were designed to presumptive myrosinase genes for bacteria. The first primer/probe combination consisted of:

```
Probe:
                                    (SEQ ID NO: 1)
5'-ATCATGTTTCTGGCATTGCGTGCC-3';

Primer 1:
                                    (SEQ ID NO: 2)
5'-GTTGATAAGCGCGTTGGTAATC-3';
and Primer 2:
                                    (SEQ ID NO: 3)
5'-CGTATCGTGGGCTGGTAAAG-3'.
```

The second primer/probe combination consisted of:

```
Probe:
                                    (SEQ ID NO: 4)
5'-CGCGCCAACCTGTAGCTCAAATTC-3';

Primer 1:
                                    (SEQ ID NO: 5)
5'-GTTCACCACCTCGCGTATATC-3';
and Primer 2:
                                    (SEQ ID NO: 6)
5'-CTTGCCGGTGGAGATGTTTA-3'.
```

PCR was performed using the PrimeTime Gene Expression master Mix Kit from IDT, Inc. (Coralville, Iowa) for the primer/probe set. *Lactobacillus plantarum* 14917 gDNA was used as a positive control. The nucleotide and amino acid sequence of the *Lactobacillus plantarum* 14917 myrosinase gene are provided as SEQ ID NO: 9 and 10, respectively). As per the manufacturer's instructions, 5 µl PrimeTime Gene Expression Master Mix (2×), 0.5 µl PrimeTime qPCR Assay (20× primer/probe), 2.0 µl DNA Template and 2.5 µl nuclease-free water were added to the reaction. Thermocycler conditions were started with a 3 min denaturation step at 95° C. followed by 40 cycles of denaturation at 95° C. for 15 seconds, annealing and elongation at 60° C. for 1 minute.

16S rRNA Sequencing: Strains selected through genetic screening were identified by sequencing the 16S rRNA gene after amplification using primers 27F-YM (5'-d{AGAGTTTGATTGGCTCAG}-3') (SEQ ID NO: 7), and 1492R-Y (5'-d{TACCTTGTTAGACTT}-3') (SEQ ID NO: 8). PCR reactions were set up in 20 µL volumes containing 2.0 µL 10λ PCR Buffer, 0.8 µL of 50 mM $MgCl_2$, 0.4 µL dNTPs (10 mM each), 0.8 of each forward and reverse primer (10 µM each), 0.08 µL Platinum Taq (Life Technologies 10966083), 2 µL template gDNA and 13.12 µL $ddH_2O$. Conditions started with a 4 minute denaturation at 95° C., followed by 35 cycles of denaturation at 95° C. for 30 seconds, annealing at 50° C. for 30 seconds and extension at 72° C. for 30 seconds before a final extension at 72° C. for 7 minutes.

Results and Discussion

Four strains were positive for the myrosinase gene. Sequencing of the 16S rRNA gene indicated that one is a *Bacillus subtilis*, another *Bacillus amyloliquefaciens*, while two additional strains are *Pediococcus pentosaceus*.

Example 2: Production of a Dietary Based Anti-Inflammatory Compound from *Bacillus subtilis* 839

*Bacillus amyloliquefaciens* 839 was identified from the studies described in Example 1 as a unique strain that can produce sulforaphane from glucoraphanin, a chemoprotective compound found in foods such as broccoli, cabbage, and kale.

In vitro studies were conducted to demonstrate the effectiveness of the myrosinase enzyme present in *Bacillus subtilis* 839. Briefly, overnight culture of *Bacillus subtilis* 839 was pelleted at 3000×g for 10 min. Cells were washed 1× with sterile peptone and spun as above. The pellet was resuspended in 10 ml minimal salts media containing 1 ml 1 mg/ml glucoraphanin and incubated 48 hr at 37° C. in an anaerobic chamber. Post incubation, a cyclocondensation reaction was performed on the supernatant. The extracted supernatant was then filter sterilized and assessed by Ultra High Performance Liquid Chromatography for detection of sulforaphane as well as reduction of glucoraphanin (FIG. 1).

Figure 2:
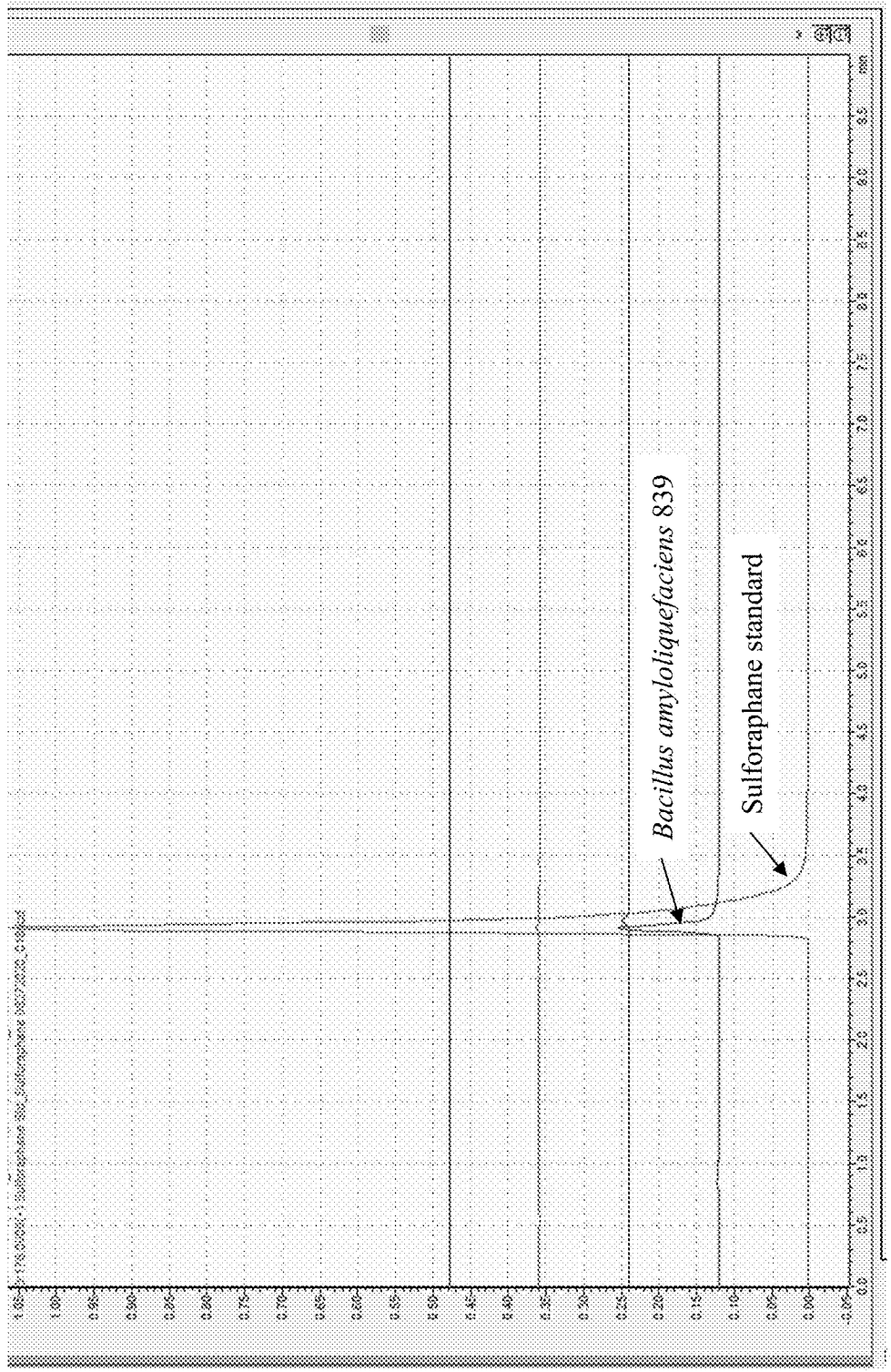
FIG. 2 shows a mass spectrometry chromatograph of sulforaphane. The second to bottom line represents the chromatograph of minimal media after 24 hours with *Bacillus subtilis* 839 in the presence of glucoraphanin. The chromatograph of *Bacillus subtilis* 839 is in alignment with the sulforaphane standard peak (bottom line).

Additional dichloromethane silica gel column extractions were performed on the 48 hr post-incubation samples as described by Campas-Baypoli, O. N. et al., 2009, *BioMed Chromatogr.* 24:387-392. The extracted supernatant was then sent to the Shimadzu Lab at the University of Wisconsin-Milwaukee to be run on the mass spectrometer for further confirmation (FIG. 2).

These findings provide support that the myrosinase enzyme identified in *Bacillus subtilis* 839 is active and converts glucoraphanin to sulforaphane.

*Bacillus* are naturally found in the gastrointestinal tract of humans and animals and many species have a long safe history of use in food preservation and production with multiple defined health benefits. Survival in the gastrointestinal tract requires a variety of attributes, including acid tolerance and the ability to withstand bile salts. In vitro assays have demonstrated that *B. subtilis* 839 is largely resistant to low pH conditions (pH 1.5 and 3.0) and survives in the presence of physiological concentrations of bile salts for extended periods of time (Table 1).

TABLE 1

Percent survivability of *Bacillus subtilis* 839 in acid and bile media at 3 hrs.

| Treatment | % survivability |
|---|---|
| pH = 1.5 | 71 |
| pH = 3.0 | 76 |
| 0.3% oxgal | 93 |

Example 3: Production of Sulforaphane by *Bacillus subtilis* CO4_4

The genome of *Bacillus subtilis* CO4_4 was sequenced with a 50.6 fold-coverage over 36 contigs with an N50 of 315,607 bp. The length of the genome is 3,918,133 bp. In vitro studies were conducted as described in Example 2 to demonstrate the effectiveness of the myrosinase enzyme present in *Bacillus subtilis* CO4_4.

Figure 3:
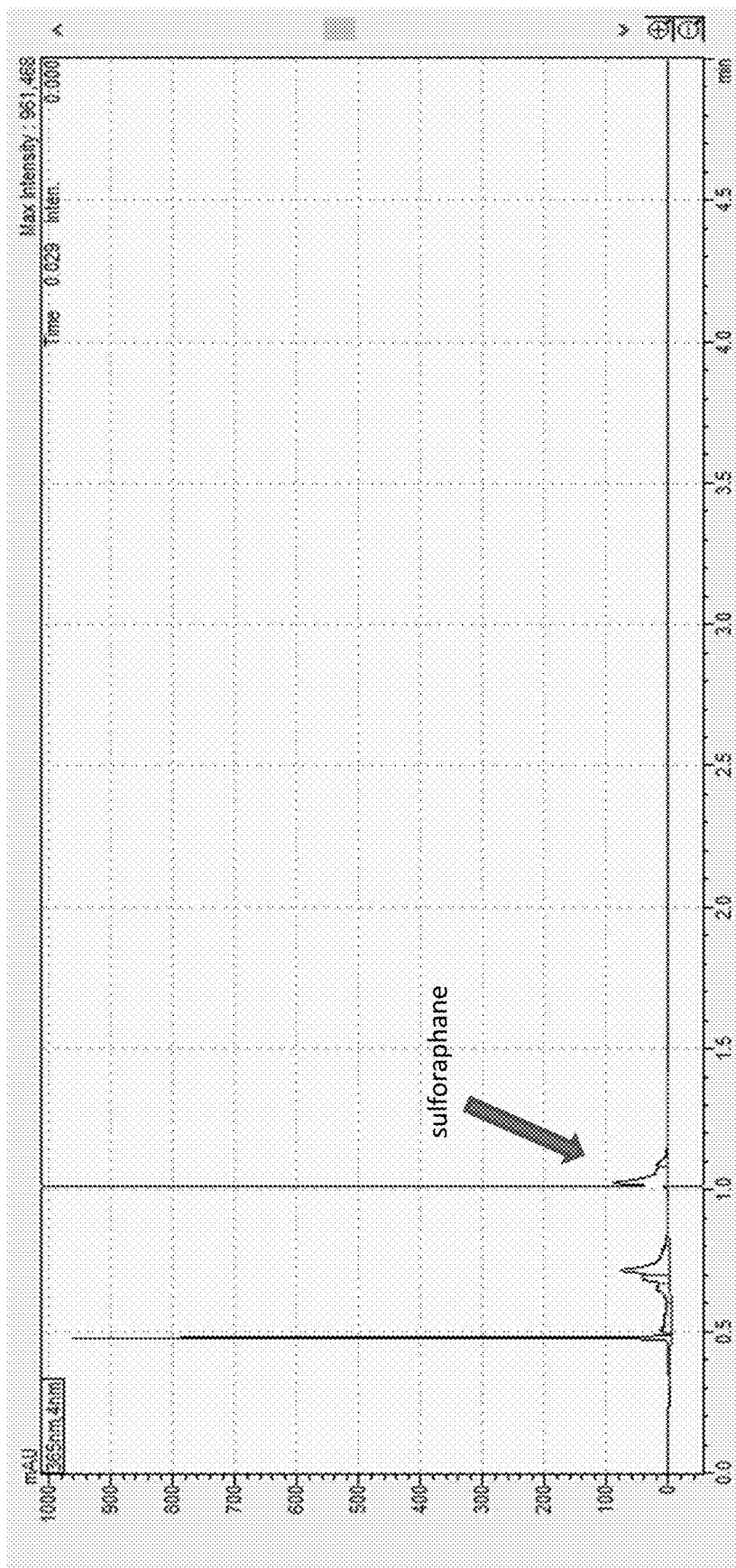
FIG. 3 provides an HPLC chromatograph of a sulforaphane cyclocondensation reaction. The black line represents the chromatograph of minimal media after 24 hours with *Bacillus subtilis* CO4_4 in the presence of glucoraphanin. The sulforaphane peak is consistent with the retention time of the sulforaphane standard after cyclocondensation.

FIG. 3 shows the HPLC chromatograph of the sulforaphane cyclocondensation reaction of minimal media after 24 hours with *Bacillus subtilis* CO4_4. The UV spectrum of the sulforaphane cyclocondensation reaction for *Bacillus subtilis* CO4_4 was similar to that of FIG. 2 for *Bacillus subtilis* 839.

These findings provide support that the myrosinase enzyme identified in *Bacillus subtilis* CO4_4 is active and converts glucoraphanin to sulforaphane.

Example 4: Human Trial

Experimental Methods

The ability of *Bacillus subtilis* 839 to increase the amount of sulforaphane in humans was tested in a Randomized, Placebo-Controlled Crossover trial of 9 individuals.

Study instructions were provided, including fasting compliance (≥10 h) prior to day 0; avoidance of any cruciferous foods for at least three days prior to days 0-9 and days 21-29; maintenance of habitual dietary practices, exercise routine, and usual body weight throughout the entire test period; and avoidance of vigorous exercise for 48 h prior to days of urine sample collection.

Briefly, three days prior to the trial participants refrained from eating foods on a provided exclusion list. On the night before the trial, participants were asked to refrain from eating anything after midnight and until the first broccoli supplement capsule was taken in the morning of the trial. Urine was collected 2 hours, 6 hours and 24 hours after taking broccoli supplement capsule. The following morning treatment capsule (*Bacillus subtilis* 839 or placebo) was taken with a glass of water on an empty stomach and treatment continued for the next 6 days. On day 7 the broccoli supplement was taken with treatment (*Bacillus subtilis* 839 or control) and urine was collected at 2 hours, 6 hours, and 24 hours after supplement. A two-week washout period followed, and the treatment regimen was repeated with the alternative treatment applied to each individual (*Bacillus subtilis* 839 or placebo)

Any adverse events (AEs), including nausea, diarrhea, upset stomach, gas, fever etc. were recorded.

Urine samples were processed by cyclocondensation reaction to preserve the sulforaphane concentrations. Samples were stored in the refrigerator until they were run on the UHPLC. The UHPLC protocol utilized an Kinetex 1.7 mm EVO C18 column and an isocratic mobile phase consisting of 80% MeOH:20% $H_2O$ (v/v), run at 0.5 ml/min. Sulforaphane was detected at 365 nm. Urine creatinine concentrations were determined by ELISA.

RESULTS

During the trial there were no adverse events related to the test product or placebo recorded and the treatment was well tolerated. One individual on the placebo arm dropped out of the trial because of a recurring illness unrelated to the trial.

Figure 4:
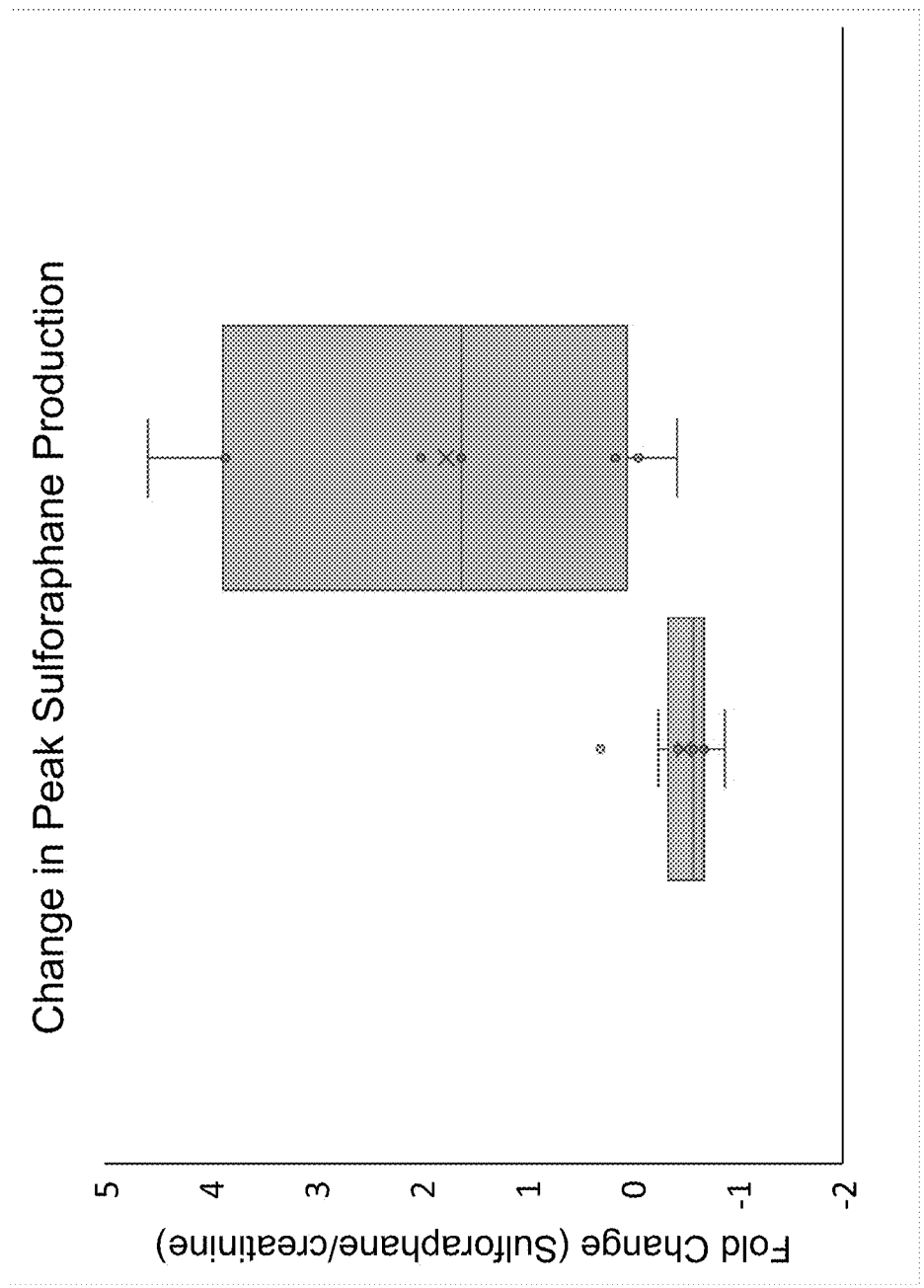
FIG. 4 provides a graph of the fold change of sulforaphane to creatinine ratio. The bar on the left represents the fold change of sulforaphane to creatinine ratio in placebo group, while the bar on the right represents the same in *Bacillus subtilis* 839 treatment group.

Urine sulforaphane concentrations were normalized to creatinine concentrations in the urine at each time point and assessed as fold change at peak production compared to that same time point during placebo. Urine sulforaphane production demonstrated high inter-individual variability among participants as is expected from the literature. However, overall a 1.76-fold increase was observed in sulforaphane production for individuals treated with *Bacillus subtilis* 839 (Figure. 4) compared to −0.50-fold change in the placebo group.

That which is claimed:

1. A method for increasing isothiocyanate production, said method comprising contacting at least one glucosinolate with an effective amount of a bacterial strain composition comprising:
   (a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
   (b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof,
   wherein said effective amount of said bacterial composition comprises about $10^8$ CFU/gram to about $10^{10}$ CFU/gram or about $10^8$ CFU/ml to about $10^{10}$ CFU/ml of said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof.

2. The method of claim 1, wherein said at least one glucosinolate comprises glucoraphanin and said isothiocyanate comprises sulforaphane.

3. The method of claim 1, wherein said bacterial strain composition comprises a capsule, gel, paste, tablet, powder, or liquid.

4. A method for increasing isothiocyanate production in a subject, said method comprising administering to a subject an effective amount of a bacterial strain composition comprising:
   (a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
   (b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof.

5. The method of claim 4, wherein said subject is administered at least one glucosinolate.

6. The method of claim 5, wherein said bacterial strain composition further comprises said at least one glucosinolate.

7. The method of claim 5, wherein said at least one glucosinolate comprises glucoraphanin and said isothiocyanate comprises sulforaphane.

8. The method of claim 5, wherein said subject is administered at least one plant, plant part, or extract thereof comprising said at least one glucosinolate.

9. The method of claim 8, wherein said extract comprises an extract from at least one cruciferous plant or plant part or wherein said at least one plant or plant part comprises at least one cruciferous plant or plant part.

10. The method of claim 4, wherein said effective amount of said bacterial composition comprises about $10^6$ CFU/gram to about $10^{10}$ CFU/gram or about $10^6$ CFU/ml to about $10^{10}$ CFU/ml of said *Bacillus subtilis* 839, *Bacillus subtilis* CO4_4, *Pediococcus pentosaceus* M3_H01, or *Pediococcus pentosaceus* M2_H12 cell, spore, or a forespore, or a combination of cells, forespores, and/or spores or the active variant of any thereof.

11. A method for increasing expression of a gene regulated by Nrf2, said method comprising contacting a cell with an effective amount of a bacterial strain composition comprising at least one glucosinolate and:
  (a) a bacterial cell of at least one of *Bacillus subtilis* 839, *Bacillus subtilis* CO4_4, *Pediococcus pentosaceus* M3_H01, or *Pediococcus pentosaceus* M2_H12, or an active variant of any thereof; and/or
  (b) at least one of a spore, or a forespore, or a combination of cells, forespores, and/or spores from any of *Bacillus subtilis* 839, *Bacillus subtilis* CO4_4, *Pediococcus pentosaceus* M3_H01, or *Pediococcus pentosaceus* M2_H12, or an active variant of any thereof.

12. The method of claim 1, wherein contacting at least one glucosinolate with the effective amount of the bacterial strain composition comprises contacting at least one plant, plant part or extract thereof comprising said at least one glucosinolate with said effective amount of said bacterial strain composition.

13. The method of claim 12, wherein said plant extract comprises an extract from at least one cruciferous plant or said at least one plant or plant part comprises a cruciferous plant or plant part.

14. The method of claim 1, comprising administering to a subject said effective amount of said bacterial strain composition, thereby contacting the at least one glucosinolate with said effective amount of said bacterial strain composition and increasing isothiocyanate production in the subject.

15. The method of claim 14, wherein said subject is administered at least one glucosinolate.

16. The method of claim 15, wherein said subject is administered at least one plant, plant part, or extract thereof comprising said at least one glucosinolate.

17. The method of claim 16, wherein said extract comprises an extract from at least one cruciferous plant or plant part or wherein said at least one plant or plant part comprises at least one cruciferous plant or plant part.

18. The method of claim 1, wherein said bacterial strain composition further comprises at least one additional bacterial strain.

19. The method of claim 18, wherein the additional bacterial strain is selected from the group consisting of a *Bacillus* spp, *Enterococcus* spp., *Bifidobacterium* spp., *Lactobacillus* spp., *Saccharomyces* spp., *Streptococcus* spp., *Propionibacterium* spp., *Megasphaera* spp., *Prevotella* spp., and *Pediococcus* spp.

20. The method of claim 1, wherein said bacterial strain composition further comprises at least one prebiotic.

* * * * *